United States Patent
Takahashi et al.

(10) Patent No.: US 12,400,324 B2
(45) Date of Patent: Aug. 26, 2025

(54) CREATION METHOD OF TRAINED MODEL, IMAGE GENERATION METHOD, AND IMAGE PROCESSING DEVICE

(71) Applicant: SHIMADZU CORPORATION, Kyoto (JP)

(72) Inventors: Wataru Takahashi, Kyoto (JP); Shota Oshikawa, Kyoto (JP); Yuichiro Hirano, Chiyoda-ku (JP); Yohei Sugawara, Chiyoda-ku (JP); Zhengyan Gao, Chiyoda-ku (JP); Kazue Mizuno, Chiyoda-ku (JP)

(73) Assignee: SHIMADZU CORPORATION, Kyoto (JP)

(*) Notice: Subject to any disclaimer, the term of this patent is extended or adjusted under 35 U.S.C. 154(b) by 248 days.

(21) Appl. No.: 17/802,303

(22) PCT Filed: Feb. 26, 2020

(86) PCT No.: PCT/JP2020/007600
§ 371 (c)(1),
(2) Date: Aug. 25, 2022

(87) PCT Pub. No.: WO2021/171394
PCT Pub. Date: Sep. 2, 2021

(65) Prior Publication Data
US 2023/0097849 A1   Mar. 30, 2023

(51) Int. Cl.
*G06K 9/00* (2022.01)
*G06T 5/50* (2006.01)
(Continued)

(52) U.S. Cl.
CPC ............. *G06T 7/0012* (2013.01); *G06T 5/50* (2013.01); *G06T 11/008* (2013.01); *G06V 10/70* (2022.01);
(Continued)

(58) Field of Classification Search
CPC ........ A61B 1/000094; A61B 1/000096; A61B 1/000095; A61B 5/1128; A61B 2576/02;
(Continued)

(56) References Cited

U.S. PATENT DOCUMENTS 6,459,457 B1 * 10/2002 Renner .................. H04N 9/642
348/638
2009/0169075 A1   7/2009 Ishida et al.
(Continued)

FOREIGN PATENT DOCUMENTS

JP   2021-513697 A   5/2021
KR   10-1981202 B1   5/2019
(Continued)

OTHER PUBLICATIONS

Written Opinion by the International Search Authority for PCT application No. PCT/JP2020/007600, dated May 12, 2020.
(Continued)

*Primary Examiner* — Avinash Yentrapati
(74) *Attorney, Agent, or Firm* — Muir Patent Law, PLLC

(57) ABSTRACT

In a creation method of a trained model, a reconstructed image (60) obtained by reconstructing three-dimensional X-ray image data (80) is generated. A projection image (61) is generated from a three-dimensional model of an image element (50) by a simulation. The projection image is superimposed on the reconstructed image to generate a superimposed image (67). A trained model (40) is created by performing machine learning using the superimposed image, and the reconstructed image or the projection image.

15 Claims, 15 Drawing Sheets

(51) Int. Cl.
  *G06T 7/00* (2017.01)
  *G06T 11/00* (2006.01)
  *G06V 10/70* (2022.01)
(52) U.S. Cl.
  CPC .............. *G06T 2207/10081* (2013.01); *G06T 2207/20221* (2013.01); *G06T 2207/30008* (2013.01); *G06T 2207/30101* (2013.01)
(58) Field of Classification Search
  CPC ........ A61B 2576/023; A61B 2576/026; G06T 7/0012; G06T 7/0014; G06T 2207/10132; G06T 2207/10136; G06T 2207/30004; G06T 2207/30008; G06T 2207/30012; G06T 2207/30016; G06T 2207/30021; G06T 2207/30024; G06T 2207/30028; G06T 2207/30032; G06T 2207/30036; G06T 2207/30041; G06T 2207/30044; G06T 2207/30048; G06T 2207/30052; G06T 2207/30056; G06T 2207/30061; G06T 2207/30064; G06T 2207/30068; G06T 2207/30076; G06T 2207/30081; G06T 2207/30084; G06T 2207/30088; G06T 2207/30092; G06T 2207/30096; G06T 2207/30101; G06T 2207/30104; G06V 2201/03; G06V 2201/031; G06V 2201/032; G06V 2201/033
  See application file for complete search history.

(56) References Cited

U.S. PATENT DOCUMENTS

| 2019/0236777 | A1* | 8/2019 | Takada .................. G06T 7/0012 |
| 2019/0259493 | A1 | 8/2019 | Xu et al. |
| 2020/0184639 | A1 | 6/2020 | Park et al. |
| 2021/0030374 | A1* | 2/2021 | Takahashi .............. A61B 6/504 |
| 2021/0042917 | A1* | 2/2021 | Hirai .................... G06V 10/751 |
| 2021/0398254 | A1 | 12/2021 | Oshikawa et al. |

FOREIGN PATENT DOCUMENTS

| WO | 2007029467 A1 | 3/2007 |
| WO | 2019138438 A1 | 7/2019 |
| WO | 2019/155306 A1 | 8/2019 |
| WO | 2019176734 A1 | 9/2019 |
| WO | 2020075531 A1 | 4/2020 |

OTHER PUBLICATIONS

First Office Action dated May 18, 2024 for corresponding Chinese Patent Application No. 202080097558.X.
Notice of Reasons for Refusal dated Apr. 16, 2024 for corresponding Japanese Patent Application No. 2022-502635.
Second Office Action dated on Jan. 27, 2025 for corresponding Chinese Patent Application No. 202080097558.X.

* cited by examiner (IMAGE ELEMENT EXAMPLE: BONE)

(IMAGE ELEMENT EXAMPLE: DEVICE)

(IMAGE ELEMENT EXAMPLE: NOISE)

(IMAGE ELEMENT EXAMPLE: BLOOD VESSEL)

(IMAGE ELEMENT EXAMPLE: CLOTHING)

(IMAGE ELEMENT EXAMPLE: SCATTERED RAY COMPONENT OF X-RAYS)

(A) PROJECTION ANGLE IN FIRST DIRECTION (B) PROJECTION ANGLE IN SECOND DIRECTION

ENERGY SPECTRUM OF X-RAYS

AVERAGE 41 keV

ENERGY SPECTRUM OF X-RAYS

AVERAGE 61 keV

CREATION METHOD OF TRAINED MODEL, IMAGE GENERATION METHOD, AND IMAGE PROCESSING DEVICE

TECHNICAL FIELD

The present invention relates to a creation method of a trained model, an image generation method, and an image processing device.

BACKGROUND ART

In the related art, a method of performing image processing using a trained model is known. Such a method is disclosed, for example, in PCT International Publication NO. WO2019/138438.

PCT International Publication NO. WO2019/138438 discloses that the conversion is performed on an X-ray image of a region including a specific part of a subject using a trained model to create an image representing the specific part. In PCT International Publication NO. WO2019/138438, a bone part of the subject, a blood vessel into which a contrast medium is injected, and a stent to be placed in a body are shown as an example of the specific part. The trained model is created by performing machine learning using a first digitally reconstructed radiography (DRR) image and a second DRR image, which are reconstructed from CT image data, as a teacher input image and a teacher output image, respectively. By differentiating the image obtained by the conversion using the trained model from an original image, it is possible to generate an image in which the specific part is removed.

CITATION LIST

Patent Literature

[PTL 1] PCT International Publication NO. WO2019/138438

SUMMARY OF INVENTION

Technical Problem

PCT International Publication NO. WO2019/138438 discloses performing, on one specific type of image element (specific part), image processing, such as creating an image representing the bone part as the specific part, creating an image representing a blood vessel into which the contrast medium is injected, and creating an image representing the stent placed in the body. However, in order to improve the visibility of medical images in various usage scenes, it is desired to enable the image processing on various image elements and even on a plurality of image elements, in addition to the image processing limited to one specific image element (specific part).

In addition, PCT International Publication NO. WO2019/138438, since the machine learning is performed using the first DRR image and the second DRR image, which are reconstructed from the CT image data, it is necessary to prepare the CT image data actually including the image element (specific part) to be extracted. In order to efficiently perform the machine learning on various image elements, it is desire to enable the machine learning without being limited to the use of the CT image data actually including the image element to be extracted, or enable the machine learning even on the image element in which it is difficult to separate and extract only the image element, although it is included in the CT image data.

The present invention has been made to solve the above-described problems, and one object of the present invention is to provide an image generation method and an image processing device capable of performing image processing on various image elements and even on a plurality of image elements, and to provide a creation method of a trained model capable of efficiently performing the creation of the trained model used for such image processing.

Solution to Problem

In order to achieve the above object, a first aspect of the present invention relates to a creation method of a trained model, the method including generating a reconstructed image obtained by reconstructing three-dimensional X-ray image data into a two-dimensional projective image, generating a two-dimensional projection image from a three-dimensional model of an image element, which is an extraction target, by a simulation, superimposing the projection image of the image element on the reconstructed image to generate a superimposed image, and creating a trained model that performs processing of extracting the image element included in an input image, by performing machine learning using the superimposed image as teacher input data and the reconstructed image or the projection image as teacher output data.

A second aspect of the present invention relates to an image generation method including separately extracting a plurality of image elements from an X-ray image using a trained model in which processing of extracting a specific image element from an input image has been learned, and generating a processed image in which image processing is performed on each image element included in the X-ray image, by performing an inter-image arithmetic operation using a plurality of extraction images extracted for the respective image elements, and the X-ray image.

A third aspect of the present invention relates to an image processing device including an image acquisition unit that acquires an X-ray image, an extraction processing unit that separately extracts a plurality of image elements from the X-ray image using a trained model in which processing of extracting a specific image element from an input image has been learned, and an image generation unit that generates a processed image in which image processing is performed on each image element included in the X-ray image, by performing an inter-image arithmetic operation using a plurality of extraction images extracted for the respective image elements, and the X-ray image.

It should be noted that, in the present specification, the "processing of extracting" the image element is a broad concept that includes both generating an image representing the extraction image element by extracting the image element, and generating the X-ray image from which the image element is removed by the extraction. More specifically, the "processing of extracting" the image element includes generating an image of only the image element and generating an image obtained by removing the image element from the original X-ray image. In addition, the "inter-image arithmetic operation" means that one image is generated by performing an arithmetic operation, such as addition, subtraction, multiplication, and division between one image and another image. More specifically, the "inter-image arithmetic operation" means that arithmetic operation processing of a pixel value is performed for each corresponding pixel between a plurality of images to decide the pixel value of the pixel in the image after the arithmetic operation.

Advantageous Effects of Invention

With the creation method of the trained model in the first aspect described above, since the superimposed image obtained by superimposing the reconstructed image obtained by reconstructing the three-dimensional X-ray image data into the two-dimensional projective image on the two-dimensional projection image generated from the three-dimensional model of the image element, which is the extraction target, by a simulation is used as the teacher input data, and the reconstructed image or the projection image is used as the teacher output data, even in a case in which the three-dimensional X-ray image data does not include the image element, which is the extraction target, it is possible to perform the machine learning using the image element, which is the extraction target, generated by the simulation. That is, teacher data can be prepared without actually preparing a CT image data including the image element to be extracted. In addition, since the projection image of the image element, which is the extraction target, is generated by the simulation, the teacher data can be prepared even for the image element that is included in the CT image data, but is difficult to be separated and extracted. As a result, it is possible to efficiently create the trained model for performing the image processing on various image elements and even on a plurality of image elements.

In addition, with the image generation method in the second aspect described above and the image processing device in the third aspect described above, since the plurality of image elements are separately extracted from the X-ray image using the trained model in which the processing of extracting the specific image element from the input image has been learned, and the processed image is generated by performing the inter-image arithmetic operation using the plurality of extraction images extracted for the respective image elements, and the X-ray image, it is possible to freely add or subtract each extraction image from the X-ray image in accordance with the type of the extraction image element after various image elements are separately extracted from the input X-ray image as the extraction images. As a result, the image processing can be performed on various image elements and even on a plurality of image elements.

DESCRIPTION OF EMBODIMENTS

Figure 1:
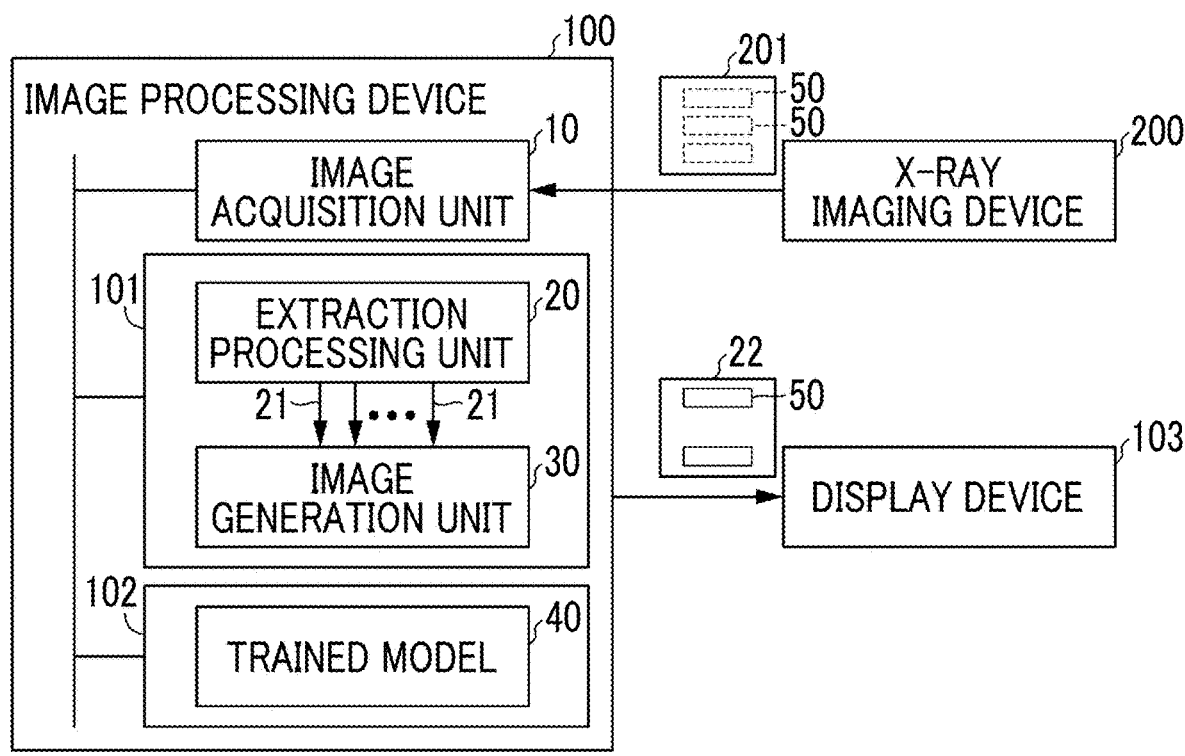
FIG. 1 is a block diagram showing an image processing device according to an embodiment.

In the following, an embodiment embodying the present invention will be described with reference to the drawings.

With reference to FIGS. 1 to 28, a configuration of an image processing device 100 according to the embodiment, an image generation method according to the embodiment, and a creation method of a trained model according to the embodiment will be described.

(Configuration of Image Processing Device)

First, the configuration of the image processing device 100 will be described with reference to FIG. 1.

The image processing device 100 is configured to extract an image element 50 included in an X-ray image 201 using a trained model 40 created through machine learning, and perform image processing of the X-ray image 201 using the extraction image element 50. The image processing device 100 generates the X-ray image 201 captured by an X-ray imaging device 200 as an input, and a processed image 22 in which the image processing is performed on each image element 50 included in the X-ray image 201 as an output.

As shown in FIG. 1, the image processing device 100 includes an image acquisition unit 10, an extraction processing unit 20, and an image generation unit 30. The image processing device 100 is configured by a computer including one or a plurality of processors 101, such as a central processing unit (CPU) and a graphics processing unit (GPU), and one or a plurality of storage units 102, such as a hard disk drive (HDD) and a solid state drive (SSD). The image processing device 100 is connected to a display device 103.

The image acquisition unit 10 is configured to acquire the X-ray image 201. The image acquisition unit 10 is configured by, for example, an interface for communicably connecting an external device and the image processing device 100. The image acquisition unit 10 may include a communication interface, such as a local area network (LAN) as an interface. The image acquisition unit 10 may include an input/output interface, such as HDMI (registered trademark), a display port, and a USB port. The image acquisition unit 10 can acquire the X-ray image 201 from the X-ray imaging device 200 or from a server device connected via a network by communication.

The X-ray image 201 is a medical image obtained by imaging a patient or a subject by the X-ray imaging device 200. The X-ray image 201 may be any a still image or a video image. The video image is a collection of still images captured at a predetermined frame rate. The X-ray image 201 is a two-dimensional image. The X-ray image 201 may be various images captured by simple X-ray imaging, fluoroscopy, angiography, and the like.

The extraction processing unit 20 is configured to separately extract a plurality of image elements 50 from the X-ray image 201 using the trained model 40 stored in the storage unit 102. The trained model 40 is a trained model in which processing of extracting a specific image element 50 from an input image has been learned.

The image element 50 is an image part or image information constituting the X-ray image 201, and is defined as a group of the same or similar types. The image element 50 may be a part of a human body that is anatomically classified. Such an image element 50 is a biological tissue, such as a bone or a blood vessel. The image element 50 may be an object introduced or placed in the body of the subject in surgery or the like. Such an image element 50 may be, for example, a device, such as a catheter, a guidewire, a stent, a surgical instrument, or fixture, which is introduced into the body. The image element 50 may be a noise, an artifact, a scattered ray component of X-rays, or the like generated during imaging processing in the X-ray imaging. The image element 50 may be clothing worn by the subject and reflected at the time of the imaging. It should be noted that the clothing is a concept including clothes, ornaments, and other attachments. For example, a button, a fastener, an accessory, a metal part, and the like of the clothing are reflected in the X-ray image 201.

The trained model 40 is created in advance through machine learning in which the processing of extracting the specific image element 50 from the input image is learned.

The extraction processing unit 20 extracts the image element 50 using one or a plurality of trained models 40. As a result, the extraction processing unit 20 generates a plurality of extraction images 21 obtained by extracting separate image elements 50 from the X-ray image 201. For example, a first extraction image 21 includes a first image element 50, and a second extraction image 21 includes a second image element 50 different from the first image element 50. The creation method of the trained model 40 will be described below.

The image generation unit 30 is configured to generate the processed image 22 in which the image processing is performed on each image element 50 included in the X-ray image 201, by performing inter-image arithmetic operation using the plurality of extraction images 21 extracted for the respective image elements 50, and the X-ray image 201. The image processing includes, for example, enhancement processing of the image element 50 or removal processing of the image element 50. It should be noted that the enhancement processing is processing of relatively increasing a pixel value of a pixel belonging to the image element 50. The removal processing is processing of relatively lowering the pixel value of the pixel belonging to the image element 50. The removal processing includes reducing the visibility by partial removal, in addition to completely removing the image from the image. In addition, the enhancement processing may be, for example, edge enhancement processing. The removal processing may be noise removal processing.

The inter-image arithmetic operation is to decide the pixel value of the corresponding pixel in the processed image 22 by performing the arithmetic operation of the pixel value for each corresponding pixel between the plurality of extraction images 21 and the X-ray image 201. A content of the arithmetic operation is not particularly limited, but may be, for example, four arithmetic operations of addition, subtraction, multiplication, and division. In the present embodiment, the inter-image arithmetic operation includes weighting addition or weighting subtraction of the individual extraction image 21 with respect to the X-ray image 201. By performing the weighting addition of the extraction image 21 with respect to the X-ray image 201, the enhancement processing of the image element 50 included in the X-ray image 201 can be performed. By performing the weighting subtraction of the extraction image 21 with respect to the X-ray image 201, the removal processing of the image element 50 included in the X-ray image 201 can be performed. By adjusting a weight value, a degree of enhancement or a degree of removal of the image element 50 can be optimized.

In the example of FIG. 1, the processor 101 functions as the extraction processing unit 20 and the image generation unit 30 by executing a program (not shown) stored in the storage unit 102. That is, in the example of FIG. 1, the extraction processing unit 20 and the image generation unit 30 are realized as functional blocks of the processor 101. The extraction processing unit 20 and the image generation unit 30 may be configured as individual hardware.

It should be noted that the individual hardware includes the extraction processing unit 20 and the image generation unit 30 configured by separate processors. The individual hardware means that a plurality of computers (PCs) in the image processing device 100, and a computer (PC) that functions as the extraction processing unit and a computer (PC) that functions as the image generation unit are separately provided.

The image processing device 100 displays, on the display device 103, the processed image 22 generated by the image generation unit 30. For example, the image processing device 100 transmits the generated processed image 22 to the server device via the network. For example, the image processing device 100 records the generated processed image 22 in the storage unit 102.

Figure 2:
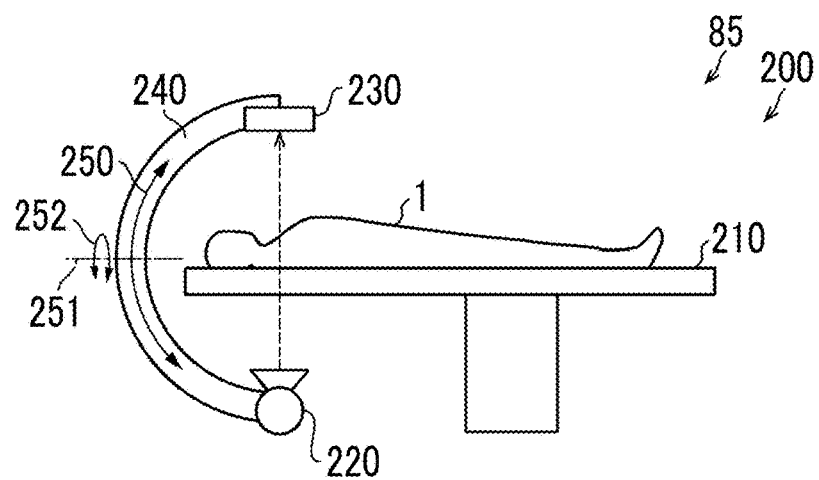
FIG. 2 is a diagram showing an example of an X-ray imaging device.

FIG. 2 shows a configuration example of the X-ray imaging device 200. FIG. 2 shows an example of a blood vessel X-ray imaging device that can perform blood vessel fluoroscopy. The X-ray imaging device 200 includes a top plate 210, an X-ray irradiation unit 220, and an X-ray detector 230. The top plate 210 is configured to support a subject 1 (person). The X-ray irradiation unit 220 includes an X-ray source, such as an X-ray tube, and is configured to emit X-rays toward the X-ray detector 230. The X-ray detector 230 is configured by, for example, a flat panel detector (FPD), and is configured to detect the X-rays emitted from the X-ray irradiation unit 220 and transmitted through the subject 1.

In the example of FIG. 2, the X-ray irradiation unit 220 and the X-ray detector 230 are held by a C-arm 240. The C-arm 240 is movable in a first direction 250 along an arm portion having an arcuate shape and is rotatable in a second direction 252 around a rotation axis 251. As a result, the X-ray imaging device 200 can change the projection direction of the X-rays from the X-ray irradiation unit 220 toward the X-ray detector 230 to the first direction 250 and the second direction 252, respectively, by a predetermined angle range.

(Trained Model)

Figure 3:
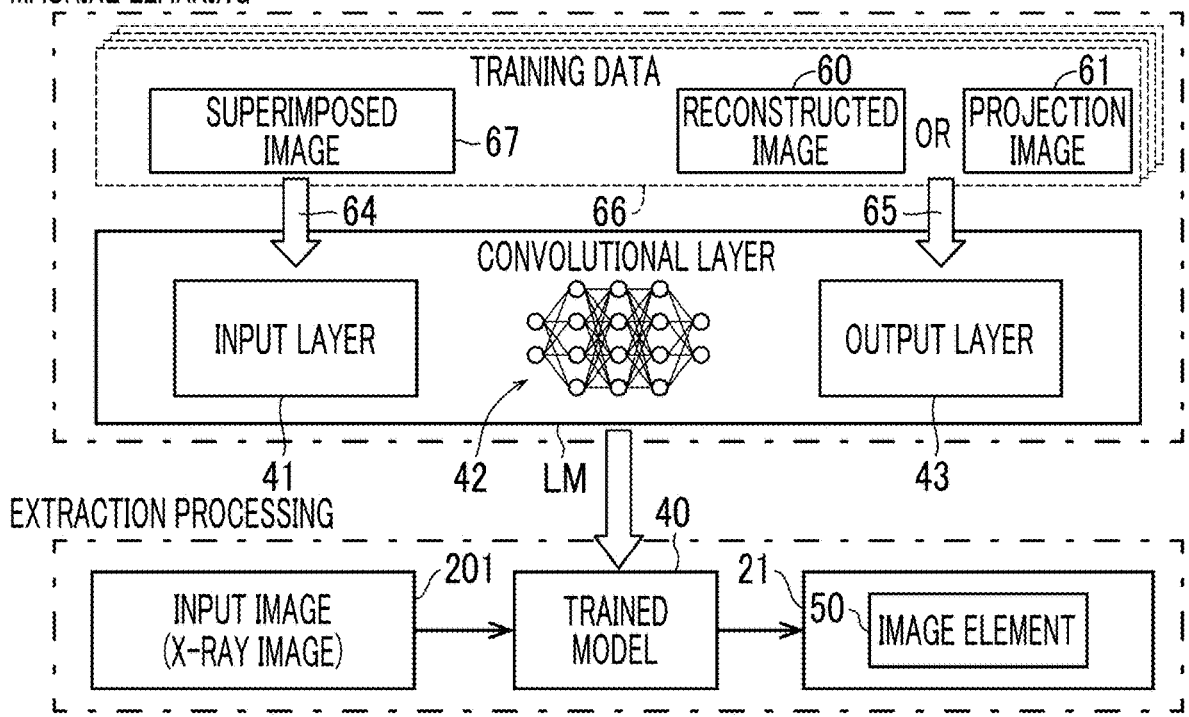
FIG. 3 is a diagram for describing machine learning with respect to a learning model, and a trained model.

As shown in FIG. 1, the processing of extracting the image element 50 included in the X-ray image 201 is performed by the trained model 40 created through the machine learning. As shown in FIG. 3, the trained model 40 extracts a pre-learned image element 50 from the input image, and outputs the extraction image 21 displaying only the extraction image element 50.

In the present embodiment, the trained model 40 is created in advance through the machine learning using a reconstructed image 60 obtained by reconstructing three-dimensional image data into a two-dimensional projective image, and a projection image 61 created from a three-dimensional model of the image element 50 by a simulation.

As a machine learning method, any method, such as fully convolutional neural networks (fully convolutional networks; FCN), a neural network, a support vector machine (SVM), or boosting, can be used. For a learning model LM (trained model 40) according to the present embodiment, it is preferable to use a convolutional neural network, and more preferably the fully convolutional neural networks. Such a learning model LM (trained model 40) includes an input layer 41 into which an image is input, a convolutional layer 42, and an output layer 43.

In order to create the trained model 40, the machine learning is performed using training data 66 including teacher input data 64 and teacher output data 65. The teacher input data 64 and the teacher output data 65 included in one training data 66 have a relationship between the data before extraction and the data after extraction for the same image element 50.

The machine learning is performed for each image element of the plurality of image elements 50 to be extracted. That is, the training data 66 is prepared for each image element 50 to be extracted.

Figure 4:
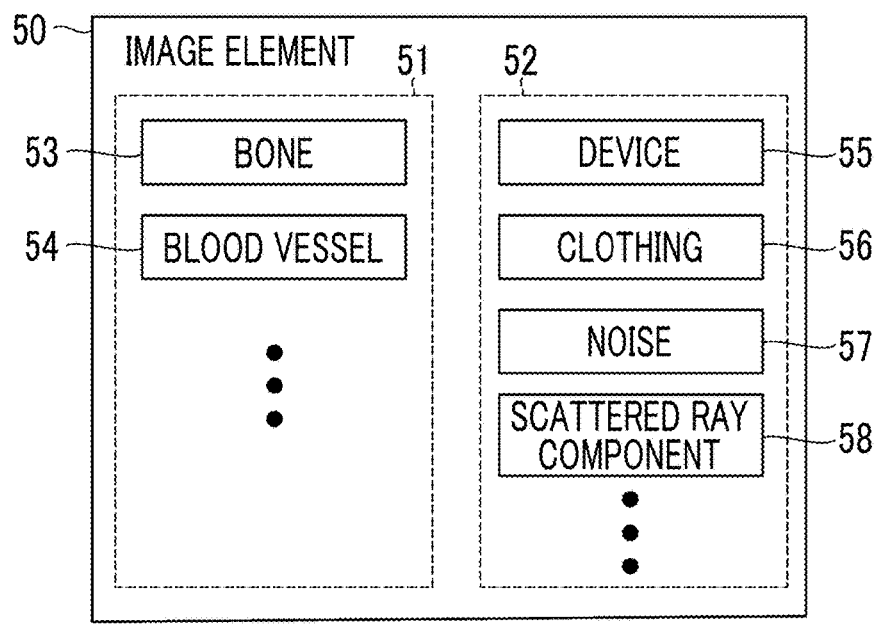
FIG. 4 is a diagram showing an example of an image element.

As shown in FIG. 4, the plurality of image elements 50 include a first element 51, which is the biological tissue, and a second element 52, which is a non-biological tissue. In addition, the plurality of image elements 50 include at least a plurality of image elements of a bone 53, a blood vessel 54, a device 55 introduced into the body, clothing 56, a noise 57, and a scattered ray component 58 of the X-rays. Among these, the bone 53 and the blood vessel 54 correspond to the first element 51. The first element 51 may include the biological tissue other than the bone 53 and the blood vessel 54. Among these, the device 55 introduced into the body, the clothing 56, the noise 57, and the scattered ray component 58 of the X-rays correspond to the second element 52. The second element 52 may include the image element other than the device 55, the clothing 56, the noise 57 and the scattered ray component 58.

Figure 5:
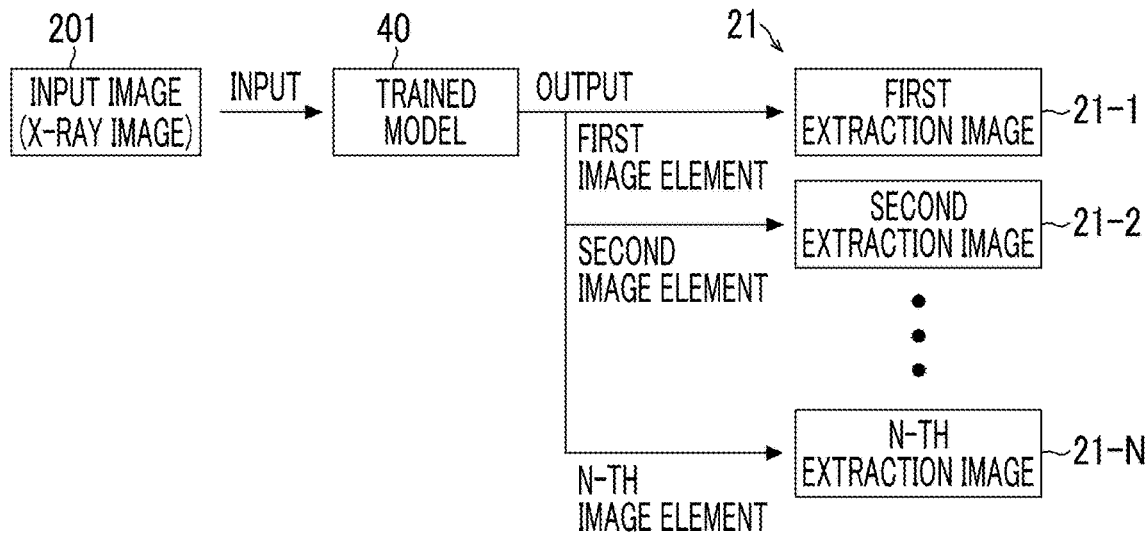
FIG. 5 is a diagram showing a first example of the extraction of the image element by the trained model.

In the example shown in FIG. 5, one trained model 40 is configured to separately extract the plurality of image elements 50. The trained model 40 has one input channel and a plurality (N) of output channels. N is an integer of 2 or more. In a case in which the X-ray image 201 is input to the input channel, the trained model 40 separately extracts N image elements 50. The trained model 40 outputs the extracted first to N-th image elements 50 as a first extraction image 21-1 to an N-th extraction image 21-N from N output channels, respectively.

Figure 6:
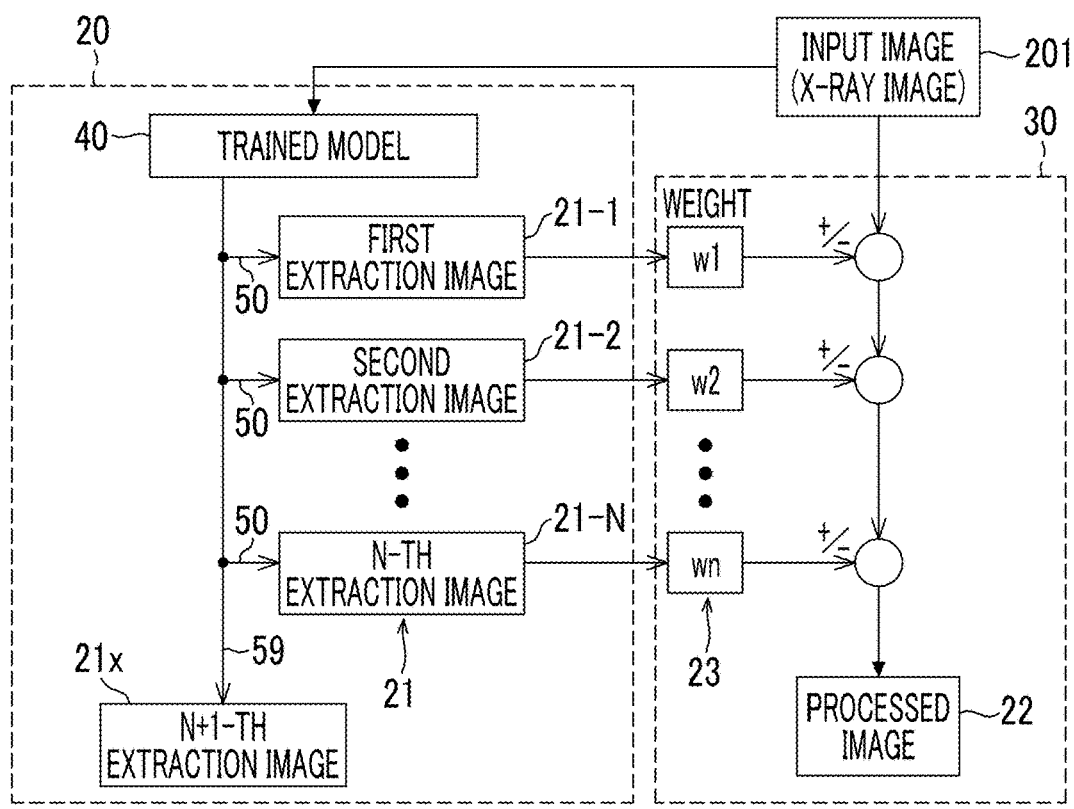
FIG. 6 is a diagram showing a second example of the extraction of the image element by the trained model and the generation of a processed image.

As an example different from FIG. 5, in the example of FIG. 6, the trained model 40 has one input channel and N+1 output channels. In a case in which the X-ray image 201 is input to the input channel, the trained model 40 extracts a plurality (N) of image elements 50 from the input image without duplication. "Without duplication" means that the image information extracted in any of the extraction images (for example, the first extraction image 21-1) is not included in other extraction images (for example, the second extraction image 21-2 to the N-th extraction image 21-N). The trained model 40 outputs the extracted first to N-th image elements as the first extraction image 21-1 to the N-th extraction image 21-N, respectively. Moreover, the trained model 40 outputs a residual image element 59 remaining after extraction as an N+1-th extraction image 21x from an N+1-th output channel.

In this case, the first extraction image 21-1 to the N-th extraction image 21-N do not include the same image information. Moreover, among the input X-ray images 201, the image information remaining without being extracted is included in the N+1-th extraction image 21x. Therefore, in a case in which the first extraction image 21-1 to the N-th extraction image 21-N and the N+1-th extraction image 21x are added, the original X-ray image 201 is returned.

As described above, in the example of FIG. 6, the trained model 40 is configured to extract the plurality of image elements 50 from the input image without duplication, and output the extracted plurality of image elements 50 and the residual image element 59 remaining after extraction, respectively. As a result, the total of the image information extracted by the extraction processing is neither increased nor decreased as compared with the input image.

As shown in FIG. 6, the image generation unit 30 (see FIG. 1) generates the processed image 22 by performing, on the input X-ray image 201, the inter-image arithmetic operation of addition or subtraction by adding a weight coefficient 23 to the first extraction image 21-1 to the N-th extraction image 21-N. The N+1-th extraction image 21x representing the residual image element 59 does not need to be used for the image processing. As the weight coefficient 23, coefficients w1 to wn are individually set corresponding to the first extraction image 21-1 to the N-th extraction image 21-N, respectively. The weight coefficient 23 may be, for example, a fixed value set in advance in the storage unit 102. It should be noted that a plurality of types of weight coefficients may be set in accordance with the intended use of the processed image 22 and the like. For example, a first setting value of the weight coefficient 23 is used for the first extraction image 21-1 in a processing mode A, and a second setting value of the weight coefficient 23 is used for the first extraction image 21-1 in a processing mode B. In addition, the weight coefficient 23 may be set to any value in accordance with the operation input of a user.

Figure 7:
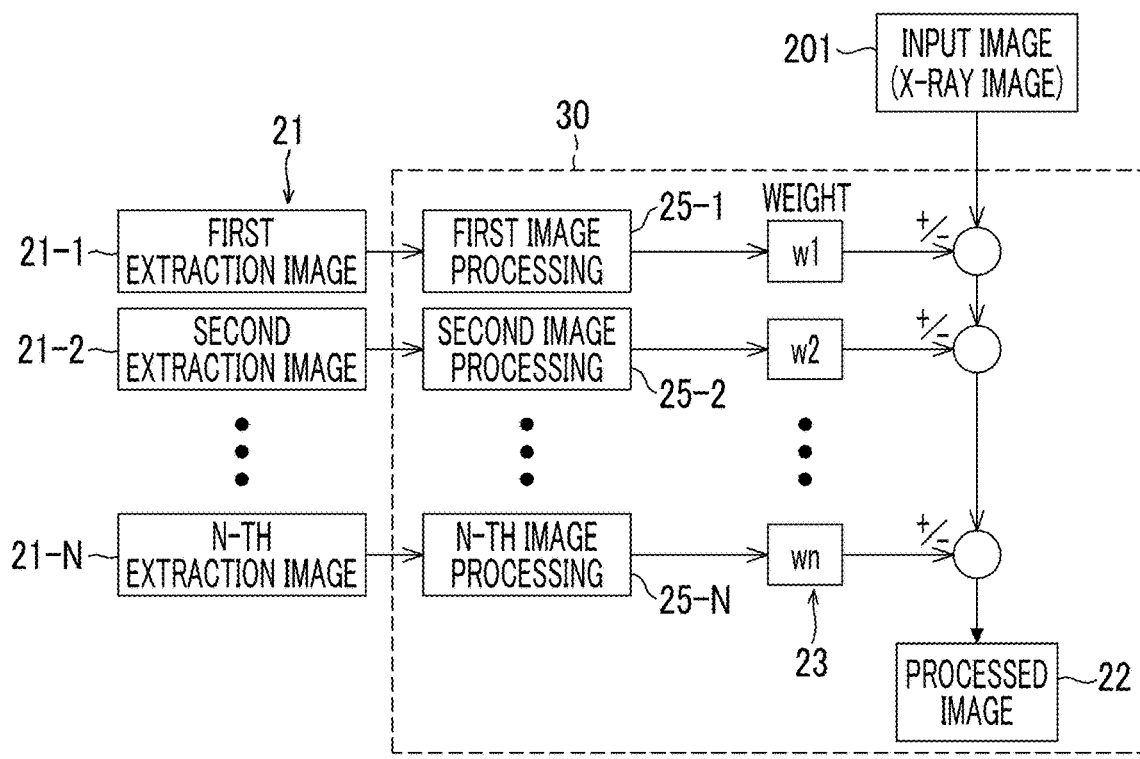
FIG. 7 is a diagram showing an example of performing image processing on an extraction image, which is different from FIG. 6.

As shown in FIG. 7, the image processing may be performed on each of the extraction images 21 before performing the inter-image arithmetic operation between each extraction image 21 and the X-ray image 201. In the example of FIG. 7, the image generation unit 30 is configured to separately perform the image processing on a part or all of the plurality of extraction images 21. The processed image 22 is generated by the inter-image arithmetic operation between the plurality of extraction images 21 after the image processing and the X-ray image 201.

For example, in FIG. 7, the image generation unit 30 performs first image processing 25-1 on the first extraction image 21-1, performs second image processing 25-2 on the second extraction image 21-2, . . . , and performs N-th image processing 25-N on the N-th extraction image 21-N. In some cases, it is not necessary to perform the image processing depending on the image element 50, and thus the image processing may be performed only on a part of the extraction images 21.

The image processing performed on the individual extraction image is not particularly limited, and may be image correction processing or image interpolation processing, for example. The image correction processing may include the edge enhancement processing and the noise removal processing. The image correction processing may be, for example, contrast adjustment, line enhancement processing, and smoothing processing. The image interpolation processing is processing of interpolating an interrupted part of the image element 50, which appears to be interrupted in the middle because it is difficult to be captured in the X-ray image 201, such as the guidewire or the catheter. In the contrast adjustment, the line enhancement processing, or the like, an appropriate parameter differs for each image element 50, and it is difficult to process all the image elements 50 at once, but the image processing is performed on the individual extraction image 21, so that the optimum image processing is performed on each image element 50.

(Image Generation Method)

Next, the image generation method according to the present embodiment will be described with reference to FIG. 8. The image generation method can be performed by the image processing device 100. The image generation method according to the present embodiment includes at least following step S2 and step S5 shown in FIG. 8.

(S2) The plurality of image elements 50 are separately extracted from the X-ray image 201 using the trained model 40 in which the processing of extracting the specific image element 50 from the input image has been learned.

(S5) The processed image 22 in which the image processing is performed on each image element 50 included in the X-ray image 201 is generated by performing the inter-image arithmetic operation using the plurality of extraction images 21 extracted for the respective image elements 50, and the X-ray image 201.

Figure 8:
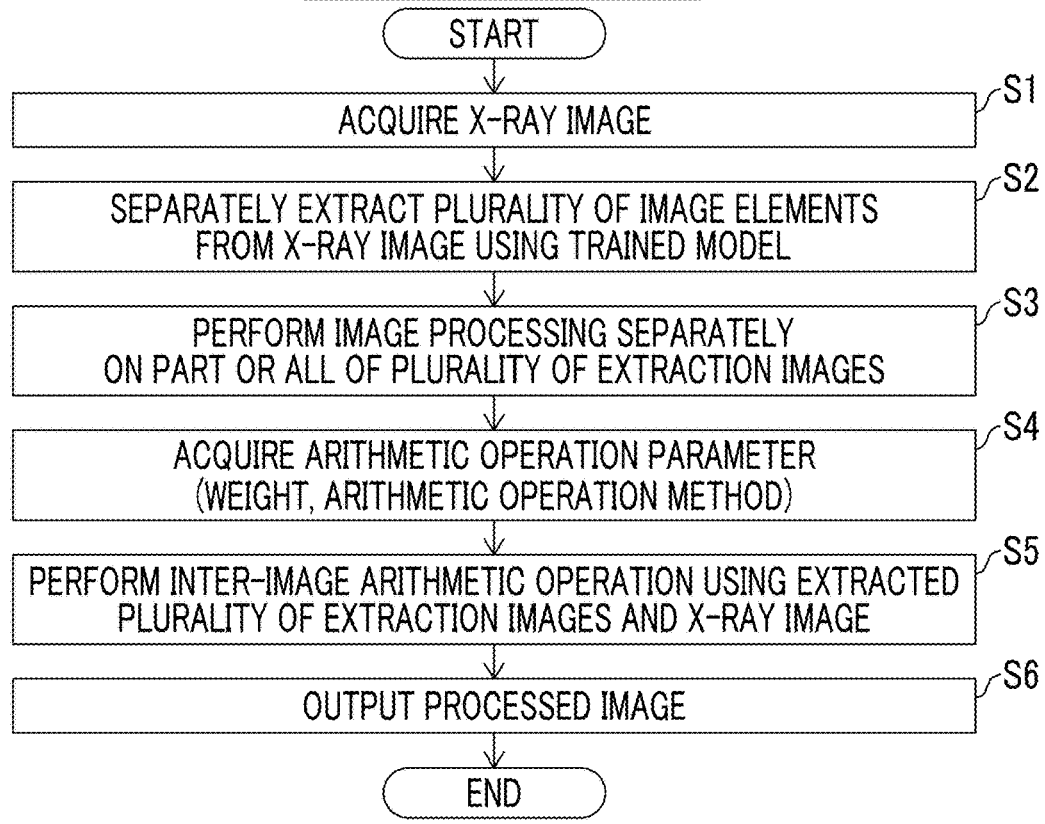
FIG. 8 is a flowchart for describing an image generation method according to the embodiment.

In addition, the image generation method according to the present embodiment may further include steps S1, S3, S4, and S6 shown in FIG. 8.

In step S1, the X-ray image 201 is acquired. Specifically, the image acquisition unit 10 (see FIG. 1) acquires the X-ray image 201 captured by the X-ray imaging device 200 shown in FIG. 2 by, for example, communication with the X-ray imaging device 200 or the server device.

In step S2, the extraction processing unit 20 separately extracts the plurality of image elements 50 from the X-ray image 201 using the trained model 40. The extraction processing unit 20 inputs the X-ray image 201 acquired in step S1 to the trained model 40. As a result, the trained model 40 outputs the first extraction image 21-1 to the N-th extraction image 21-N as shown in FIG. 5 or FIG. 6.

In step S3, as shown in FIG. 7, the image processing may be performed on a part or all of the extracted plurality of extraction images 21. In this case, the image generation unit 30 performs preset image processing on the extraction image 21, which is a target of the image processing, with a predetermined parameter. Whether or not to perform the image processing may be decided in accordance with the input from the user. Whether or not to perform the image processing may be decided in accordance with an image quality of the extraction image 21. Step S3 does not have to be performed.

In step S4, the image generation unit 30 acquires an arithmetic operation parameter for each extraction image 21. The arithmetic operation parameters include, for example, a setting value of the weight coefficient 23 and a setting value of an arithmetic operation method. The setting value of the arithmetic operation method represents whether to perform the weighting addition (that is, the enhancement processing of the image element 50) or to perform the weighting subtraction (that is, the removal processing of the image element 50) for the extraction image 21, which is the target. The setting value of the arithmetic operation method and the setting value of the weight coefficient 23 are preset in the storage unit 102 for each type of the image element 50 to be extracted.

In step S5, the image generation unit 30 performs the inter-image arithmetic operation using the plurality of extraction images 21 extracted for the respective image elements 50, and the X-ray image 201. The image generation unit 30 performs the inter-image arithmetic operation in accordance with the parameters acquired in step S4. The image generation unit 30 multiplies each of the first extraction image 21-1 to the N-th extraction image 21-N by the corresponding weight coefficient 23, and performs the inter-image arithmetic operation on the X-ray image 201 by the corresponding arithmetic operation method. As a result, the X-ray image 201 subjected to the weighting addition or the weighting subtraction by each extraction image 21 is generated as the processed image 22. As a result, the image generation unit 30 generates the processed image 22 (see FIG. 6 or 7) in which the image processing, which is the enhancement processing or the removal processing, is performed on each image element 50 included in the X-ray image 201.

In step S6, the image processing device 100 outputs the processed image 22. The image processing device 100 outputs the processed image 22 to the display device 103 or the server device. In addition, the image processing device 100 stores the processed image 22 in the storage unit 102.

After displaying the processed image 22 on the display device 103, the image generation unit 30 may receive the operation input of changing the arithmetic operation parameters. For example, the image generation unit 30 may receive the input of the value of the weight coefficient 23, or may receive the selection of another preset parameter. For example, the image generation unit 30 may receive the change in the parameters of the image processing in step S3.

Moreover, the image generation unit 30 may regenerate the processed image 22 using the changed parameters in accordance with the operation input of the user.

(Creation Method of Trained Model)

Next, the creation method of the trained model will be described. The trained model 40 may be created by the processor 101 of the image processing device 100, but may be performed using a computer for the machine learning (learning device 300, see FIG. 10).

Figure 9:
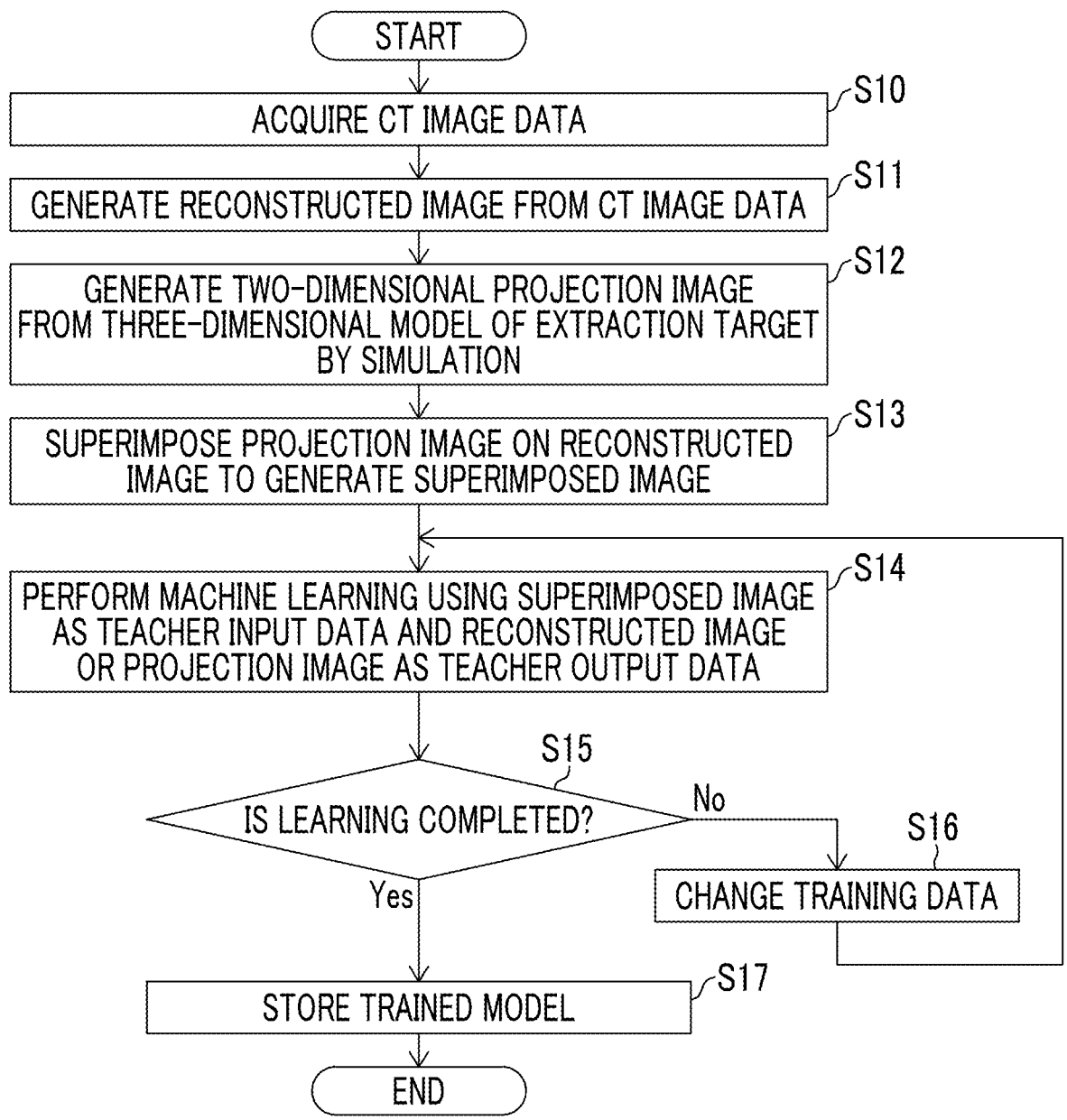
FIG. 9 is a flowchart for describing a creation method of the trained model according to the embodiment.
Figure 10:
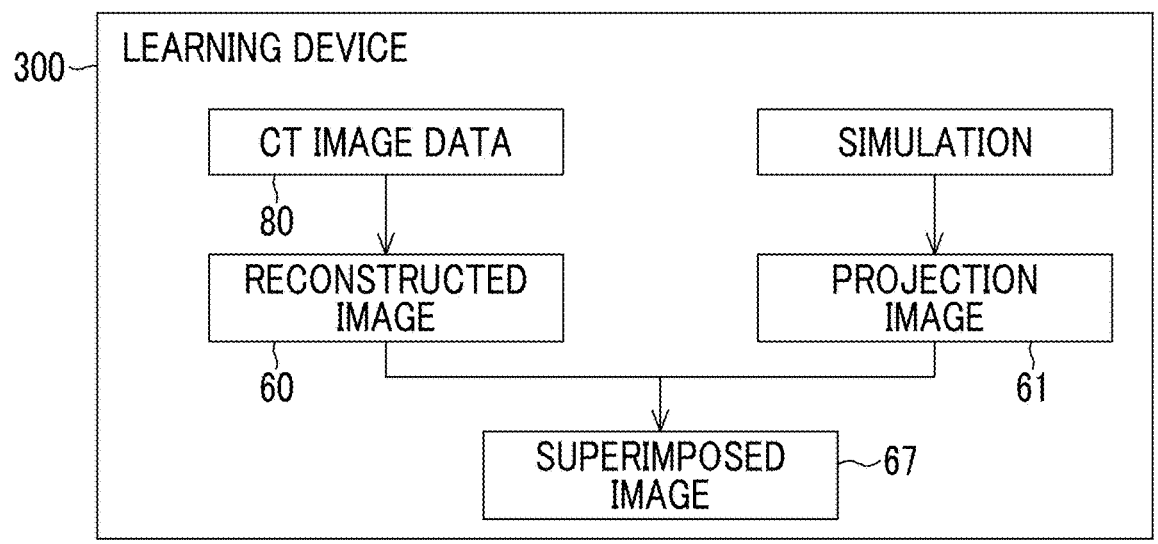
FIG. 10 is a diagram for describing the generation of a superimposed image used for the machine learning.

As shown in FIGS. 9 and 10, the creation method of the trained model according to the present embodiment includes following steps S11 to S14.

(S11) The reconstructed image 60 obtained by reconstructing computer tomography (CT) image data 80 into a two-dimensional projective image is generated. The CT image data 80 is an example of "three-dimensional X-ray image data".

(S12) The two-dimensional projection image 61 is generated from the three-dimensional model of the image element 50, which is the extraction target, by a simulation.

(S13) The projection image 61 of the image element 50 is superimposed on the reconstructed image 60 to generate a superimposed image 67.

(S14) The trained model 40 (see FIG. 3) that performs the processing of extracting the image element 50 included in the input image is created by performing the machine learning using the superimposed image 67 as the teacher input data 64 (see FIG. 3) and the reconstructed image 60 or the projection image 61 as the teacher output data 65 (see FIG. 3).

In the present embodiment, the machine learning includes inputting the teacher input data 64 (see FIG. 3) and the teacher output data 65 (see FIG. 3) created for each image element 50 to one learning model LM. The machine learning may be performed on a separate learning model LM for each image element 50, which is the extraction target.

First, in step S10 of FIG. 10, the CT image data 80 is acquired. The CT image data 80 is three-dimensional image data that reflects a three-dimensional structure of the subject 1 obtained by capturing the CT image of the subject 1. The CT image data 80 is a three-dimensional aggregate of voxel data including three-dimensional position coordinates, and a CT value at the position coordinates. For the image element of a moving (beating) part, such as the blood vessel, four-dimensional 4D-CT data including temporal change in three-dimensional information may be used. As a result, it is possible to accurately perform learning even in a case in which a target moves with time.

In step S11, the reconstructed image 60 obtained by reconstructing the CT image data 80 into the two-dimensional projective image is generated.

The reconstructed image 60 is a DRR image generated from the CT image data 80. The DRR image is a simulated X-ray image created as the two-dimensional projective image by virtual fluoroscopic projection simulating geometrical projection conditions of the X-ray irradiation unit 220 and the X-ray detector 230 of the X-ray imaging device 200 as shown in FIG. 2.

Figure 11:
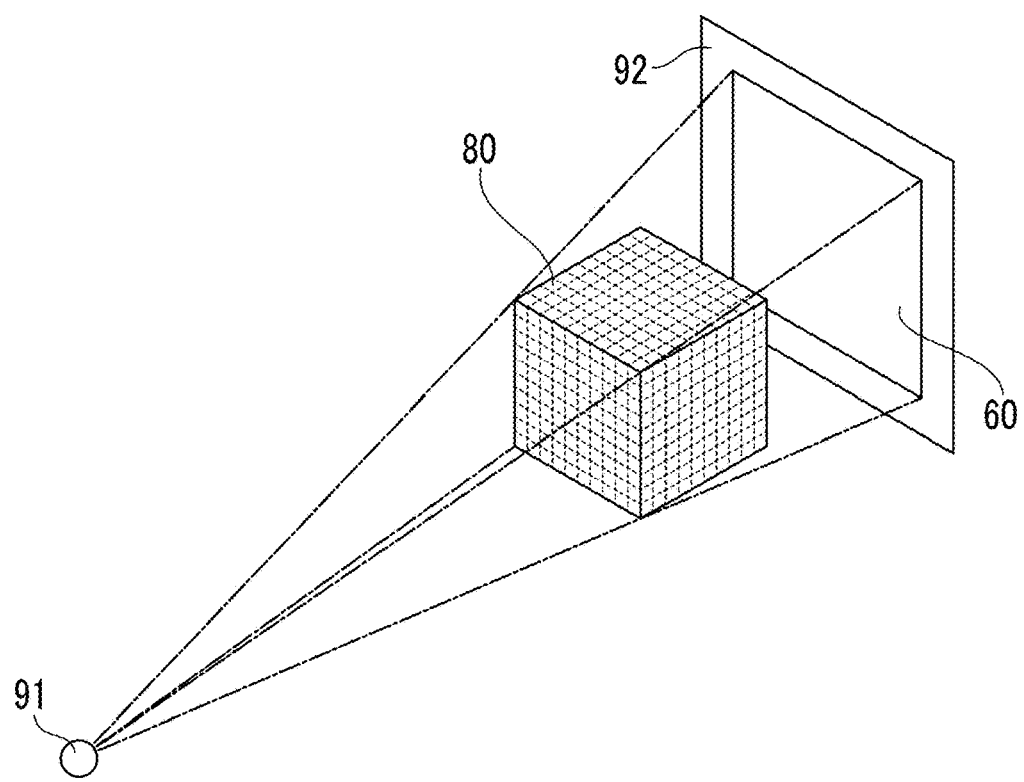
FIG. 11 is a diagram for describing a generation method of a reconstructed image.

Specifically, as shown in FIG. 11, by virtually disposing, in a three-dimensional virtual space, a virtual X-ray tube 91 and a virtual X-ray detector 92 in a predetermined projection direction with respect to the CT image data 80, a three-dimensional spatial disposition (imaging geometry) of a virtual X-ray imaging system is generated. The disposition of the CT image data 80, the virtual X-ray tube 91, and the virtual X-ray detector 92 has the same imaging geometry as the disposition of the actual subject 1, the X-ray irradiation unit 220, and the X-ray detector 230 shown in FIG. 2. It should be noted that the imaging geometry means a geometrical disposition relationship between the subject 1, the X-ray irradiation unit 220, and the X-ray detector 230 in the three-dimensional space.

Moreover, by adding the total of the CT values in the voxels in which the X-rays emitted from the virtual X-ray tube 91 have passed until reaching the virtual X-ray detector 92, the pixel value of each pixel in the reconstructed image 60 is calculated. By changing the imaging geometry, it is possible to generate the simulated X-ray image at any projection angle.

In the creation method of the trained model, the learning device 300 generates a plurality of reconstructed images 60 from one three-dimensional data (CT image data 80). The number of the generated reconstructed images 60 may be, for example, about 100,000. The learning device 300 generates the plurality of reconstructed images 60 by making the parameters, such as a projection angle, a projection coordinate, a parameter for DRR image generation, a contrast, and the edge enhancement, different from each other. The plurality of reconstructed images 60 that are made different from each other may be generated by, for example, an algorithm that randomly changes the parameters described above to generate the reconstructed image 60.

In the present embodiment, since the superimposed image 67 superimposed on the projection image 61 including the image element 50 is created, the reconstructed image 60 does not have to include the image element 50, which is the extraction target, or does not have to have an extractable contrast even in a case in which the image element 50 is included.

In addition, in the present specification, the terms "random" and "random number" mean non-regularity and a non-regular sequence (set of numbers), but it does not have to be completely random, but includes pseudo random and a pseudo random number.

In step S12 of FIG. 9, the two-dimensional projection image 61 is generated from the three-dimensional model of the image element 50, which is the extraction target, by a simulation.

The projection image 61 is the two-dimensional image representing the image element 50, which is the target of extraction by the trained model 40. The projection image 61 includes only the image element 50, for example. The learning device 300 acquires the three-dimensional model of the image element 50, which is the extraction target, and generates the projection image 61 from the three-dimensional model by a simulation.

The three-dimensional model is created, for example, by capturing the CT image of a target object including the image element 50, which is the extraction target, and extracting the image element 50 from the obtained CT data. The three-dimensional model may be created using, for example, a CT image database published by a research institution and the like. As the CT image database, for example, as a lung CT image data set, there is the lung image data base consortium and image data base resource initiative (LIDC/IDRI) by the national cancer institute of the United States. In addition to this, a brain CT image data set, a standardized three-dimensional model of the skeleton, or the like may be used. In addition, the device 55 and the clothing 56 may be created using three-dimensional CAD data. The three-dimensional model is, for example, three-dimensional image data including only the image element 50, which is the extraction target.

It should be noted that, it is not necessary to generate all the projection images 61 used for the machine learning from the three-dimensional model by a simulation. The projection image 61 may be created by acquiring the two-dimensional data (X-ray image) actually including the image element 50 to be extracted, and separating and extracting the image element 50 included in the acquired image.

The learning device 300 generates a plurality of two-dimensional projection images 61 by making parameters, such as a projection direction, a translation amount, a rotation amount, a deformation amount, and a contrast, different from each other with respect to a three-dimensional model or two-dimensional data. The plurality of projection images 61 may be generated by an algorithm that performs processing of randomly changing variable parameters, such as the translation amount, the rotation amount, the deformation amount, and the contrast, with respect to the original data (three-dimensional model, two-dimensional data, or other projection images 61).

The learning device 300 generates the plurality of two-dimensional projection images 61 for each type of the image element 50. The learning device 300 generates the plurality of projection images 61 from one original data (three-dimensional data, two-dimensional data, or projection image 61). The number of the projection images 61 generated from one original data may be, for example, about 100,000.

In step S13, the projection image 61 generated in step S12 is superimposed on the reconstructed image 60 generated in step S11 to generate the superimposed image 67 (see FIG. 10). By superimposition, the superimposed image 67 including, in the two-dimensional reconstructed image 60, the projection image 61 of the image element 50 to be extracted is generated. By combining the plurality of reconstructed images 60 and the plurality of projection images 61, a plurality of superimposed images 67 are also generated. One training data 66 (see FIG. 3) includes the superimposed image 67, and any of the reconstructed image 60 and the projection image 61 used to generate the superimposed image 67.

The machine learning is performed in step S14 of FIG. 9. The superimposed image 67 is used as the teacher input data 64 input to the input layer 41 of the learning model LM of FIG. 3. Moreover, the reconstructed image 60 or the projection image 61 is used as the teacher output data 65 input to the output layer 43 of the learning model.

In a case in which the teacher output data 65 is the reconstructed image 60, the learning model LM is trained to extract the image element 50 from the input image and generate the extraction image 21 not including the image element 50. In a case in which the teacher output data 65 is the projection image 61, the learning model LM is trained to extract the image element 50 from the input image and generate the extraction image 21 representing the extraction image element 50. The extraction image 21 may be an image including only the image element 50. It should be noted that since the image including only the extraction image element 50 can be generated by generating the processed image 22 not including the image element 50 and performing the subtraction from the input X-ray image 201, adopting the reconstructed image 60 adopting the projection image 61 as the teacher output data 65 can be considered equivalent from the viewpoint of the image processing.

It should be noted that, it is not necessary to create all the training data 66 used for the machine learning from the superimposed image 67. The reconstructed image 60 actually including the image element 50 to be extracted may be used as the teacher input data 64, and the projection image 61 of the image element 50 extracted from the reconstructed image 60 may be used as the teacher output data 65.

In step S15 of FIG. 9, the learning device 300 determines whether or not the machine learning is completed. For example, the learning device 300 determines that the machine learning is completed in a case in which the machine learning is performed a predetermined number of iterations for all the training data 66. For example, the learning device 300 determines that the machine learning is completed in a case in which a value of an evaluation function for evaluating the performance of the learning model LM is equal to or more than a predetermined value. In a case in which it is determined that the machine learning is not completed, the learning device 300 changes the training data 66 in the step S16, and performs the machine learning of the step S14 using the next training data 66.

In a case in which the machine learning is completed, the trained learning model LM is stored as the trained model 40 in step S17. As a result, the creation of the trained model 40 is completed. The created trained model 40 is recorded via the network or in a non-transitory recording medium and provided to the image processing device 100.

(Specific Example for Each Image Element)

Next, a specific example of the superimposed image 67 (teacher input data 64), and the reconstructed image 60 or the projection image 61 (teacher output data 65) for each image element 50 will be described. In addition, an example of the processed image 22 using the extraction image 21 for each image element 50 will be described.

<Bone Part>

Figure 12:
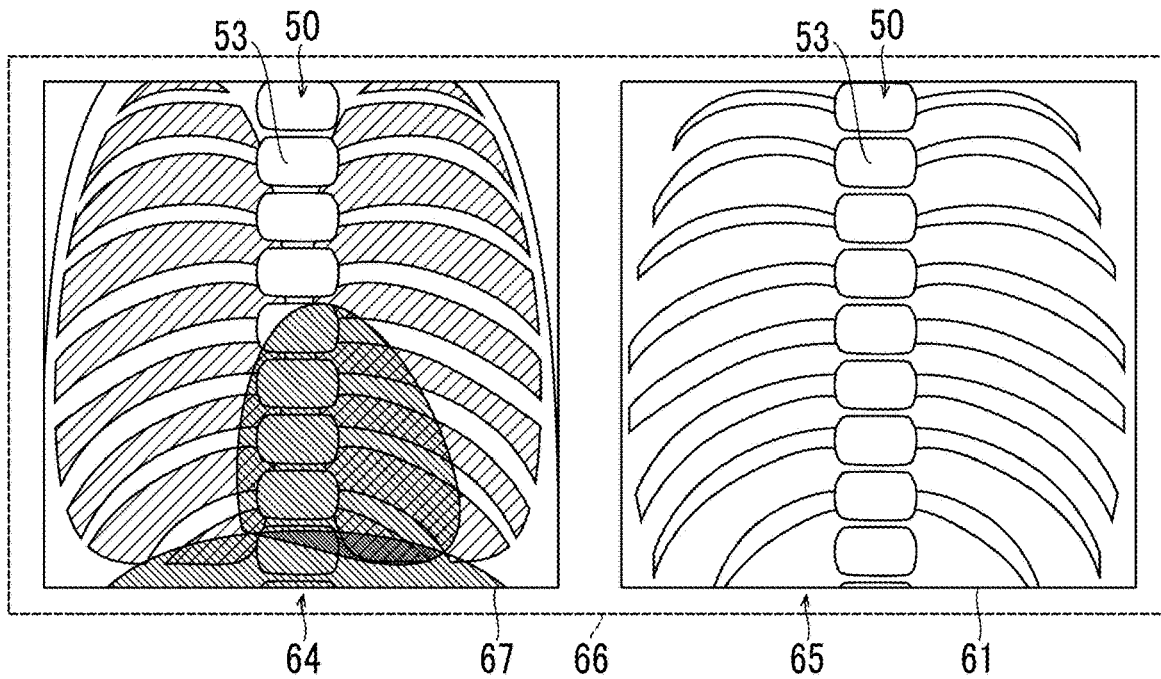
FIG. 12 is a diagram showing an example of teacher input data and teacher output data in a case in which the image element is a bone.

FIG. 12 shows an example in which the image element 50 is the bone 53. The teacher input data 64 is, for example, the superimposed image 67 of the reconstructed image 60 not including the bone 53, and the projection image 61 including the bone 53.

For example, the superimposed image 67 is generated by creating the projection image 61 from the CT image data 80 or the three-dimensional model of the skeleton and superimposing the projection image 61 on the reconstructed image 60 from which the bone 53 is removed. The reconstructed image 60 from which the bone 53 is removed is generated by clipping (fixing) the CT value to zero for the pixels in a range of the CT value of the bone 53. Since the CT value of the bone part is generally about 200 HU to about 1000 HU, a threshold value need only be set to a predetermined value of about 0 HU to 200 HU.

The teacher output data 65 is the projection image 61 including only the bone 53. As the teacher output data 65, the projection image 61 used to generate the superimposed image 67 is used.

It should be noted that, since the CT image data 80 obtained by imaging the subject usually includes the bone part, the reconstructed image 60 generated from the CT image data 80 may be used as the teacher input data 64. Therefore, it is not always necessary to create the superimposed image 67.

In this case, the teacher output data 65 is the reconstructed image 60 including only the bone 53. For example, the reconstructed image 60 including only the bone 53 is generated by clipping the CT value to zero for the pixels having the CT value less than the CT value of the bone 53 among the reconstructed images 60 including the bone 53.

Through the machine learning, the learning model LM is trained to generate the extraction image 21 in which the bone 53 is extracted, such as the teacher output data 65, from the input image, such as the teacher input data 64.

Figure 13:
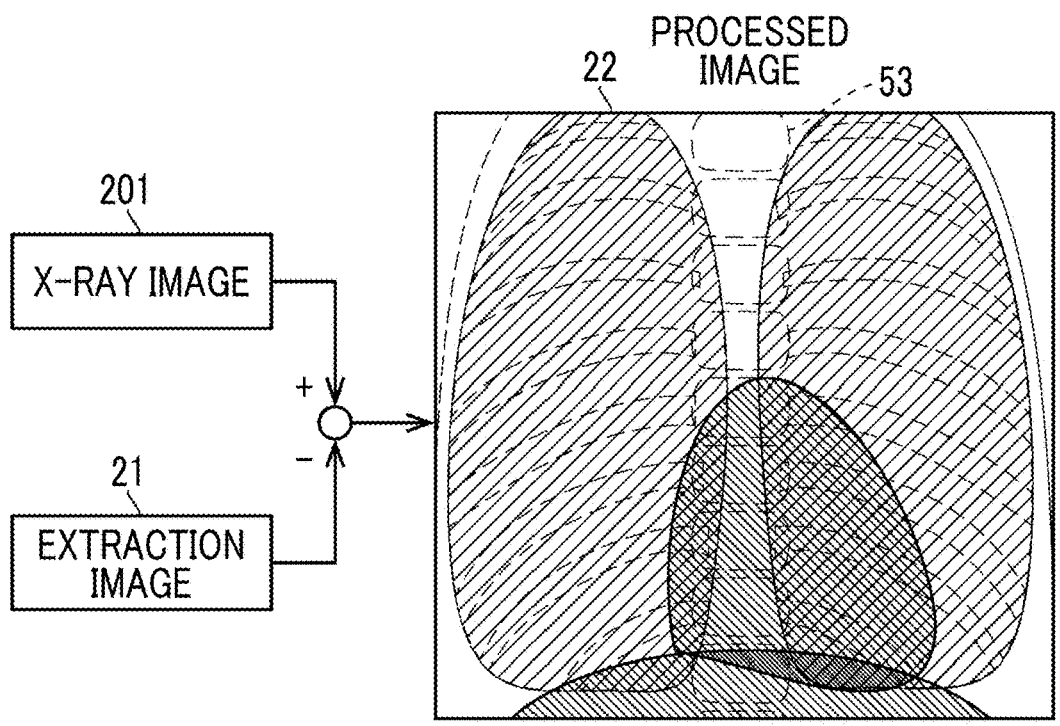
FIG. 13 is a diagram showing an example of the processed image in a case in which the image element is the bone.

The image processing device 100 performs the weighting subtraction of the extraction image 21 generated by the trained model 40 on the X-ray image 201 acquired by the X-ray imaging device 200. As a result, as shown in FIG. 13, the processed image 22 in which the image element 50 of the bone 53 from the X-ray image 201 is removed is generated. In FIG. 13, for convenience of description, the removed image element 50 of the bone 53 is shown by a broken line.

<Device>

Figure 14:
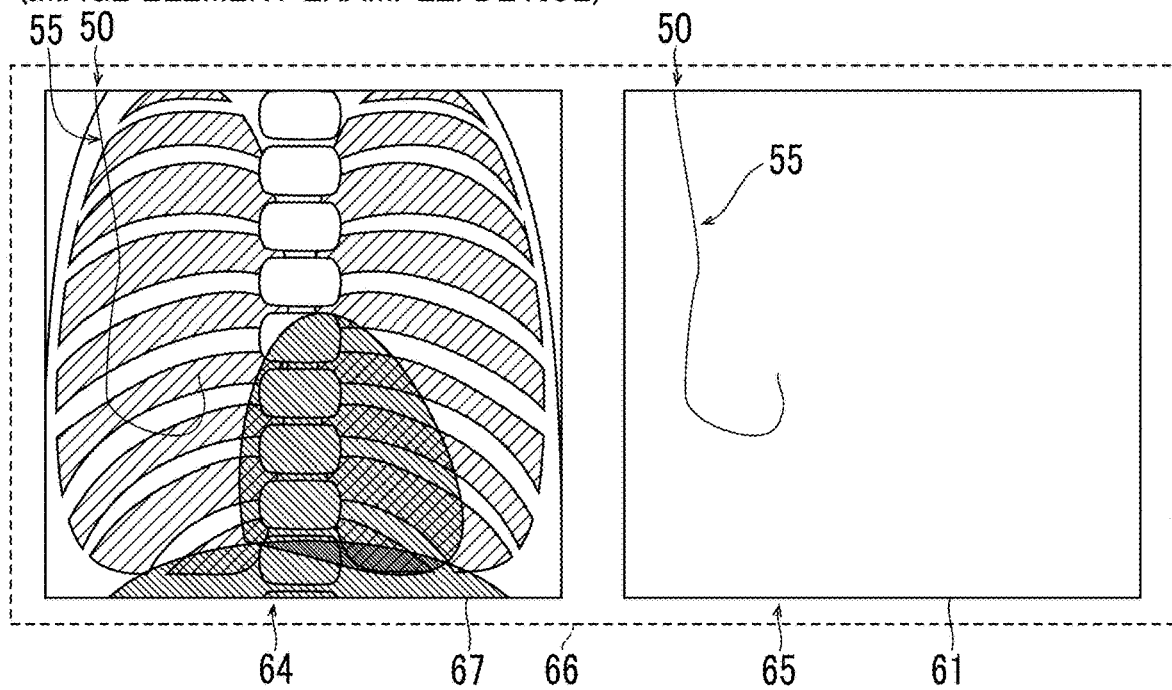
FIG. 14 is a diagram showing an example of the teacher input data and the teacher output data in a case in which the image element is a device.

FIG. 14 shows an example in which the image element 50 is the device 55. In FIG. 14, the device 55 is the guidewire.

The teacher input data 64 is the superimposed image 67 including the device 55. The image element 50 is not included in the reconstructed image 60 generated from the CT image data 80. The projection image 61 of only the device 55 generated from a three-dimensional model of the device 55 is superimposed on the reconstructed image 60. As a result, the superimposed image 67 including the device 55 is generated as shown in FIG. 14.

As described above, a plurality of variations of the projection image 61 of which the shape and the like are changed by a simulation may be created by capturing a two-dimensional X-ray image of the device 55. The plurality of superimposed images 67 are generated using the plurality of projection images 61.

Figure 16:
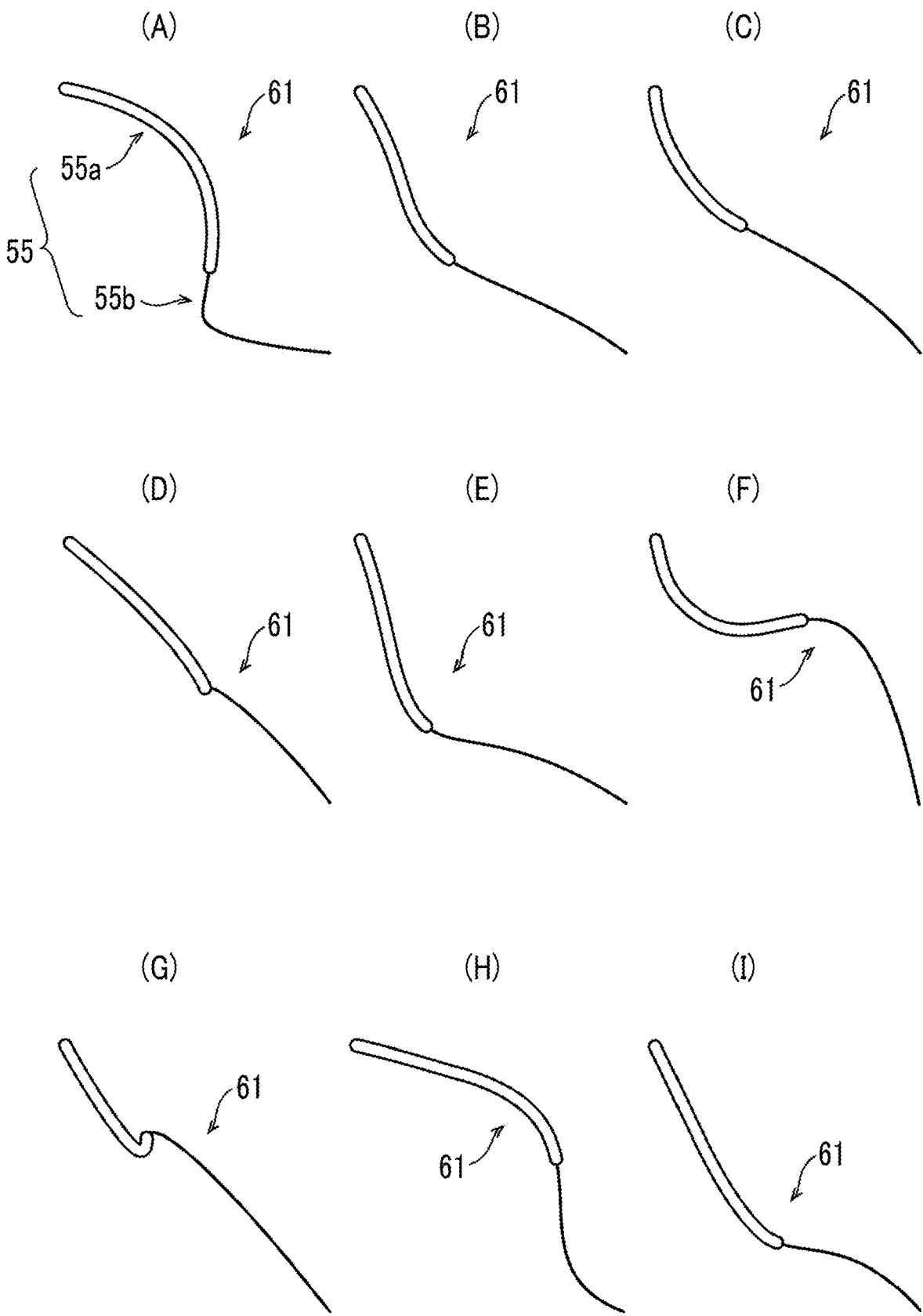
FIG. 16 is a diagram showing variations (A) to (I) of a projection image of the device generated from a three-dimensional model.

In particular, as shown in FIG. 16, in a case in which the image element 50 is the device 55 having a linear shape or a tubular shape, the projection image 61 of the image element 50 is generated by simulating a shape of the three-dimensional model of the device 55 with a curve generated based on a random coordinate value. FIG. 16 shows examples (A) to (I) in which the projection image 61 of a guidewire 55b holding a stent 55a as an example of the device 55 is generated in a random shape by curve simulation.

The guidewires 55b in the projection images 61 are generated into different shapes by a Bezier curve with the random coordinate value as a base point. The Bezier curve is a K−1 order curve obtained from K control points (K is an integer of 3 or more). A large number of the projection images 61 of the devices 55 having various shapes can be generated by an algorithm that randomly designates the coordinate values of K control points.

The plurality of single projection images 61 of the stent 55a placed in the body are generated by applying random translation, rotation, deformation, and contrast change to a three-dimensionally modeled pseudo stent.

Returning to FIG. 14, the teacher output data 65 is the projection image 61 including only the device 55. As the teacher output data 65, the projection image 61 used to generate the superimposed image 67 is used.

Through the machine learning, the learning model LM is trained to generate the extraction image 21 in which the device 55 is extracted, such as the teacher output data 65, from the input image, such as the teacher input data 64.

Figure 15:
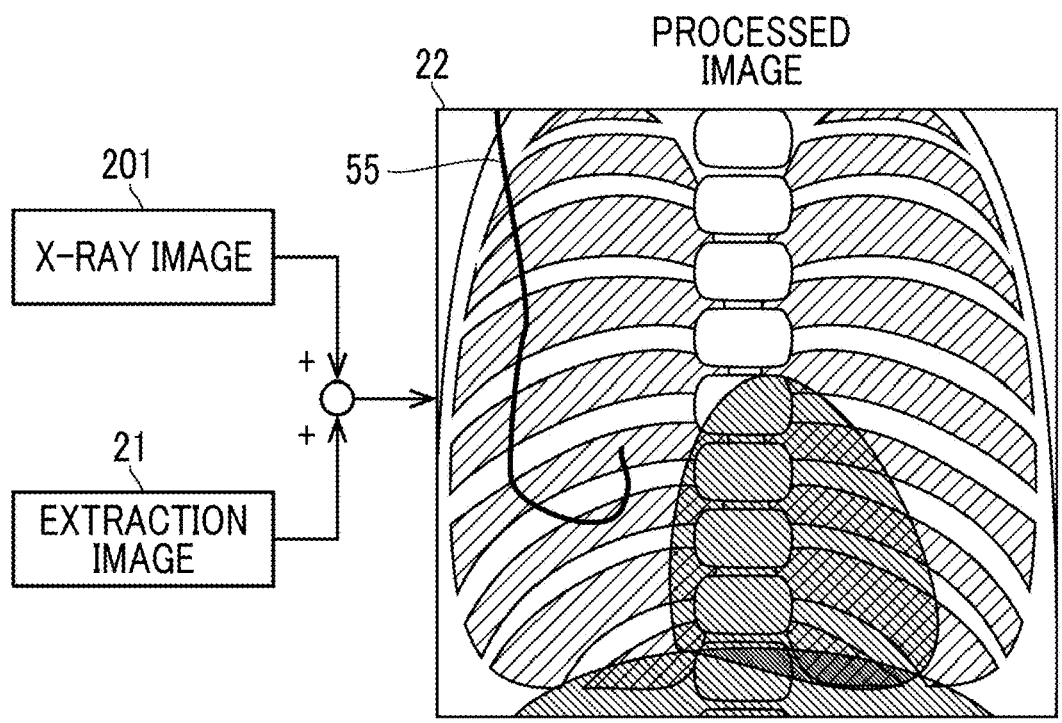
FIG. 15 is a diagram showing an example of the processed image in a case in which the image element is the device.

The image processing device 100 performs the weighting addition of the extraction image 21 generated by the trained model 40 on the X-ray image 201 acquired by the X-ray imaging device 200. As a result, as shown in FIG. 15, the processed image 22 in which the image element 50 of the device 55 is enhanced from the X-ray image 201 is generated. FIG. 15 shows that the device 55 is enhanced by showing the device 55 thicker than that of FIG. 14. The enhancement processing may include processing of coloring and displaying the image element 50 of the device 55 by the image processing before the inter-image arithmetic operation shown in FIG. 7, in addition to processing of increasing the pixel value.

<Noise>

Figure 17:
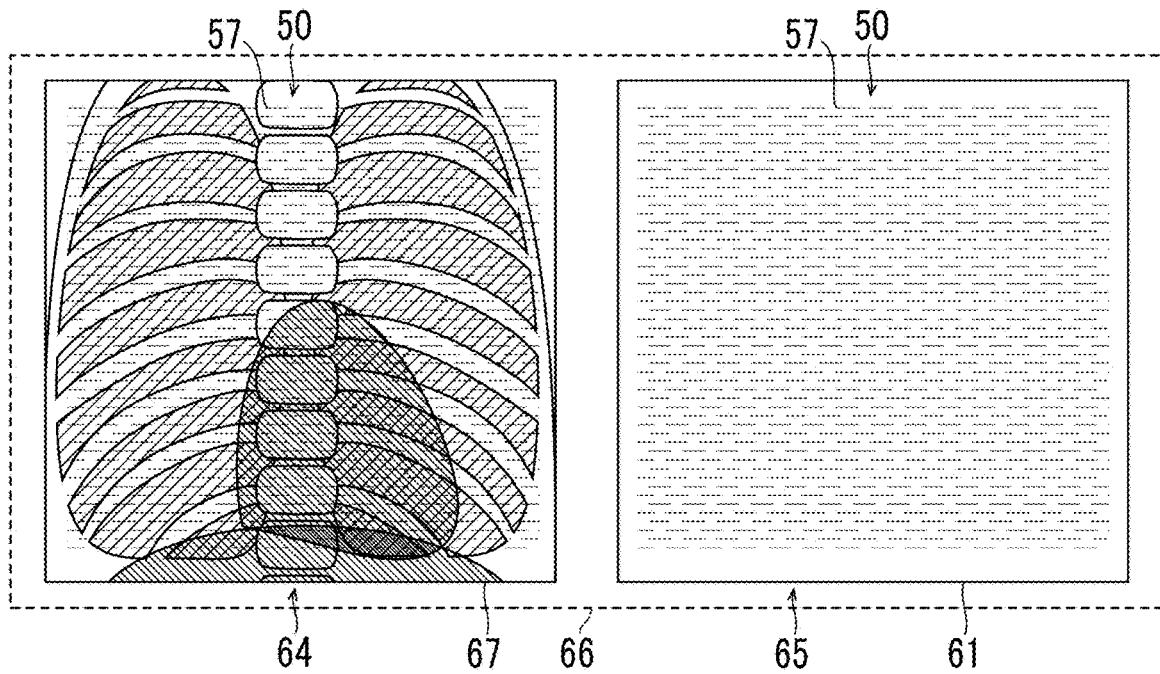
FIG. 17 is a diagram showing an example of the teacher input data and the teacher output data in a case in which the image element is a noise.

FIG. 17 shows an example in which the image element 50 is the noise 57. The noise 57 is, for example, a random noise, but is shown in FIG. 17 as a set of horizontal dotted lines for convenience of description.

The teacher input data 64 is the superimposed image 67 including the noise 57. The noise 57 is not included in the reconstructed image 60 generated from the CT image data 80. The projection image 61 including only the randomly generated noise 57 is superimposed on the reconstructed image 60. As a result, the superimposed image 67 including the noise 57 is generated as shown in FIG. 17. The noise 57 is created by randomly generating a Gaussian noise that follows a Gaussian distribution or a Poisson noise that follows a Poisson distribution for each projection image 61.

The teacher output data 65 is the projection image 61 including only the noise 57. As the teacher output data 65, the projection image 61 used to generate the superimposed image 67 is used.

Through the machine learning, the learning model LM is trained to generate the extraction image 21 in which the noise 57 is extracted, such as the teacher output data 65, from the input image, such as the teacher input data 64.

Figure 18:
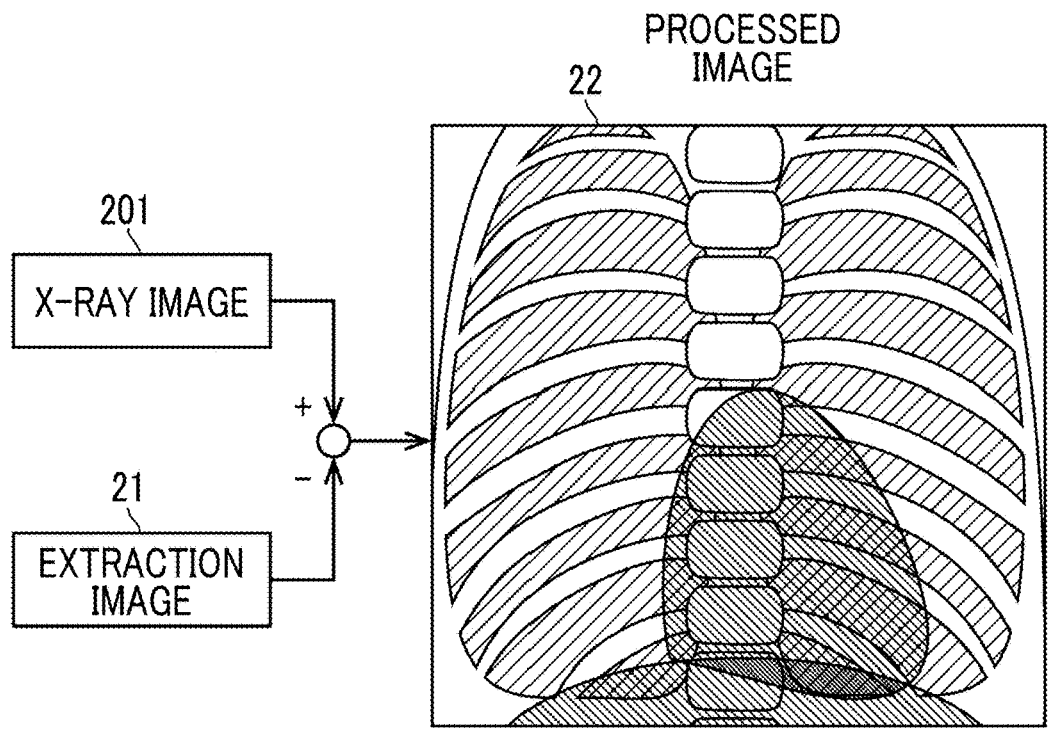
FIG. 18 is a diagram showing an example of the processed image in a case in which the image element is the noise.

The image processing device 100 performs the weighting subtraction of the extraction image 21 generated by the trained model 40 on the X-ray image 201 acquired by the X-ray imaging device 200. As a result, as shown in FIG. 18, the processed image 22 in which the image element 50 of the noise 57 is removed from the X-ray image 201 is generated. The processed image 22 of FIG. 18 shows that the noise 57 is removed from the X-ray image 201 including the noise 57 as in the teacher input data 64 of FIG. 17.

<Blood Vessel>

Figure 19:
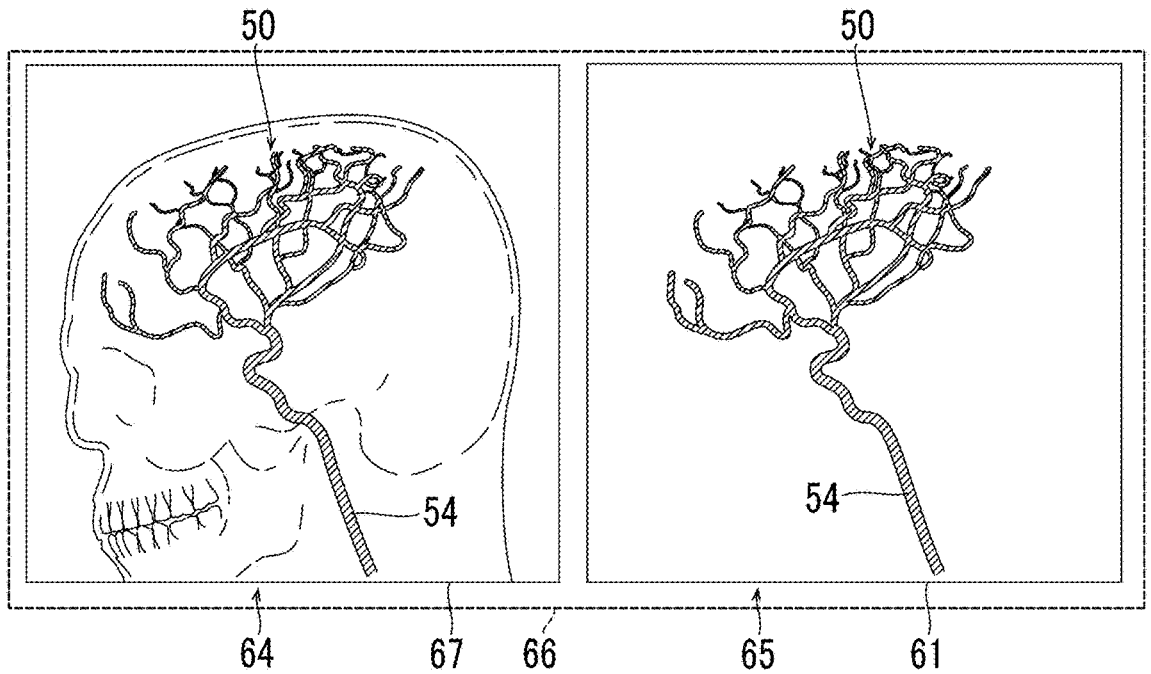
FIG. 19 is a diagram showing an example of the teacher input data and the teacher output data in a case in which the image element is a blood vessel.

FIG. 19 shows an example in which the image element 50 is the blood vessel 54. The blood vessel 54 is a contrast-imaged blood vessel imaged by introducing the contrast medium. FIG. 19 shows an example of a cerebral blood vessel in the head, but another blood vessel may be used. The blood vessel may be, for example, a coronary artery of the heart.

The teacher input data 64 is the superimposed image 67 including the blood vessel 54. The reconstructed image 60 generated from the CT image data 80 captured without the contrast includes almost no blood vessels 54 (does not have sufficient contrast). The projection image 61 of only the blood vessel 54 generated from a three-dimensional model of the blood vessel 54 is superimposed on the reconstructed image 60. As a result, the superimposed image 67 including the blood vessel 54 is generated as shown in FIG. 19.

In a case in which the image element 50 is the blood vessel 54, the projection image 61 of the image element 50 is generated by a simulation that randomly changes a shape of the three-dimensional model of the blood vessel 54. The blood vessel of the projection image 61 is subjected to random translation, rotation, deformation, contrast change, and the like by a simulation. That is, similar to the device 55 shown in FIG. 16, variations of the projection image 61 of the blood vessel 54 to which a random change is applied are generated. As described above, the projection image 61 of the blood vessel 54 may be created from the CT image data of the contrast-imaged blood vessel captured by the angiography.

The teacher output data 65 is the projection image 61 including only the blood vessel 54. As the teacher output data 65, the projection image 61 used to generate the superimposed image 67 is used.

Through the machine learning, the learning model LM is trained to generate the extraction image 21 in which the blood vessel 54 is extracted, such as the teacher output data 65, from the input image, such as the teacher input data 64.

Figure 20:
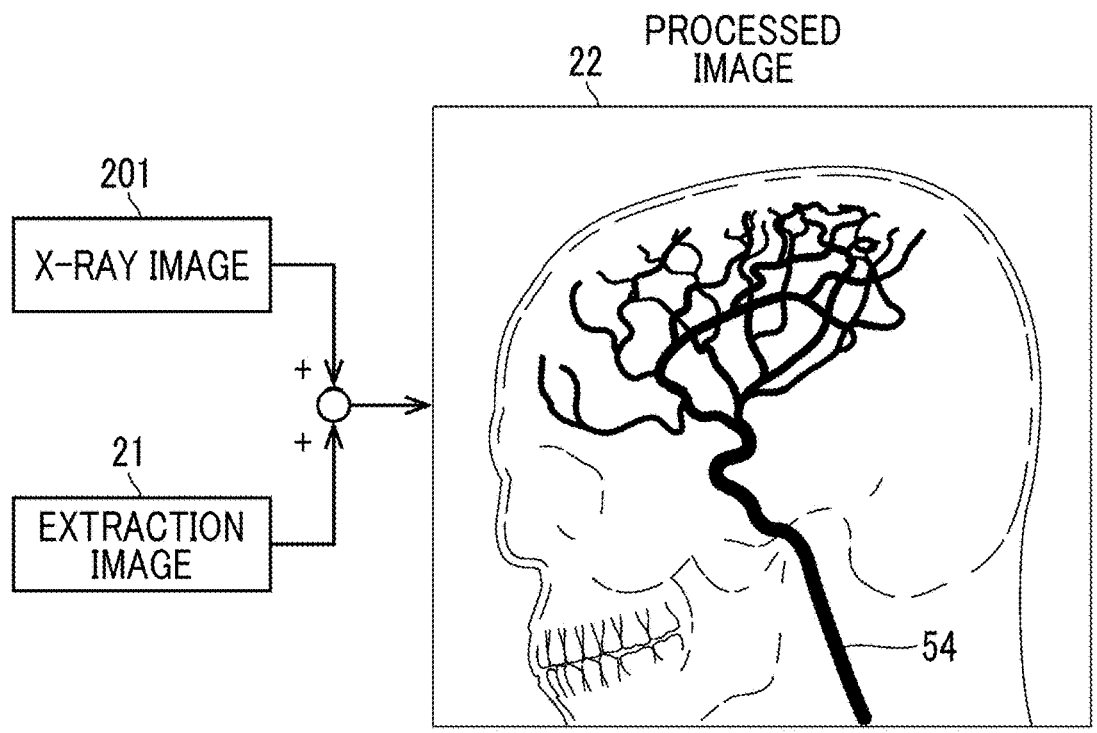
FIG. 20 is a diagram showing an example of the processed image in a case in which the image element is the blood vessel.

The image processing device 100 performs the weighting addition of the extraction image 21 generated by the trained model 40 on the X-ray image 201 acquired by the X-ray imaging device 200. As a result, as shown in FIG. 20, the processed image 22 in which the image element 50 of the blood vessel 54 is enhanced from the X-ray image 201 is generated. The processed image 22 of FIG. 20 shows that the blood vessel 54 is enhanced and displayed in the X-ray image 201 including the image element 50 of the blood vessel 54 as in the teacher input data 64 of FIG. 19.

<Clothing>

Figure 21:
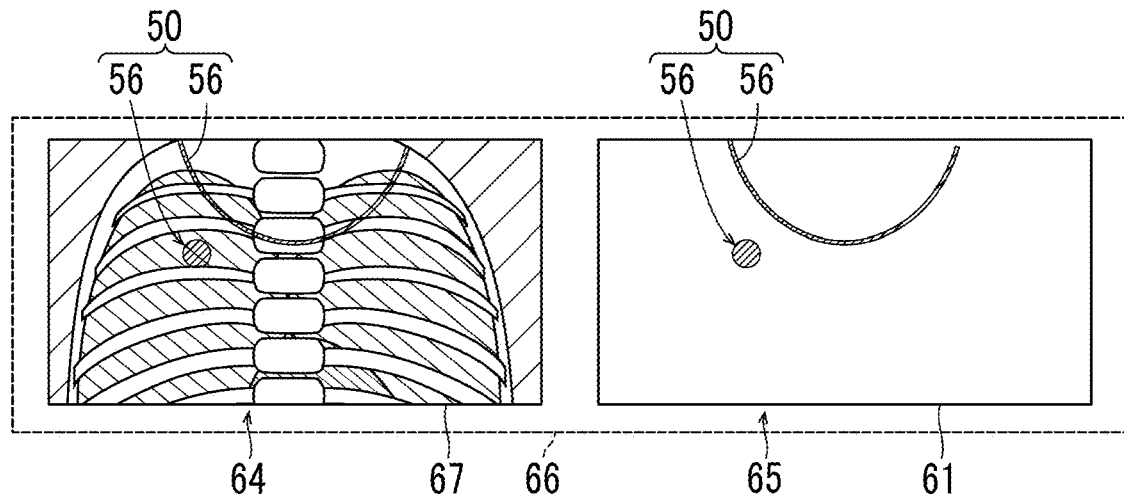
FIG. 21 is a diagram showing an example of the teacher input data and the teacher output data in a case in which the image element is clothing.

FIG. 21 shows an example in which the image element 50 is the clothing 56. FIG. 21 shows, as an example of the clothing 56, a button on the clothes and a necklace worn by the subject.

The teacher input data 64 is the superimposed image 67 including the clothing 56. The clothing 56 is not included in the reconstructed image 60 generated from the CT image data 80. The projection image 61 of only the clothing 56 generated from a three-dimensional model of the clothing 56 is superimposed on the reconstructed image 60. As a result, the superimposed image 67 including the clothing 56 is generated as shown in FIG. 21. A three-dimensional model of the clothing 56 may be created from the CT image of only the clothing 56, or may be created from, for example, the CAD data. As described above, a two-dimensional X-ray image of the clothing 56 may be captured and used as the projection image 61. The projection image 61 is subjected to random translation, rotation, deformation, contrast change, and the like by a simulation.

The teacher output data 65 is the projection image 61 including only the clothing 56. As the teacher output data 65, the same data as the projection image 61 used to generate the superimposed image 67 is used.

Through the machine learning, the learning model LM is trained to generate the extraction image 21 in which the clothing 56 is extracted, such as the teacher output data 65, from the input image, such as the teacher input data 64.

Figure 22:
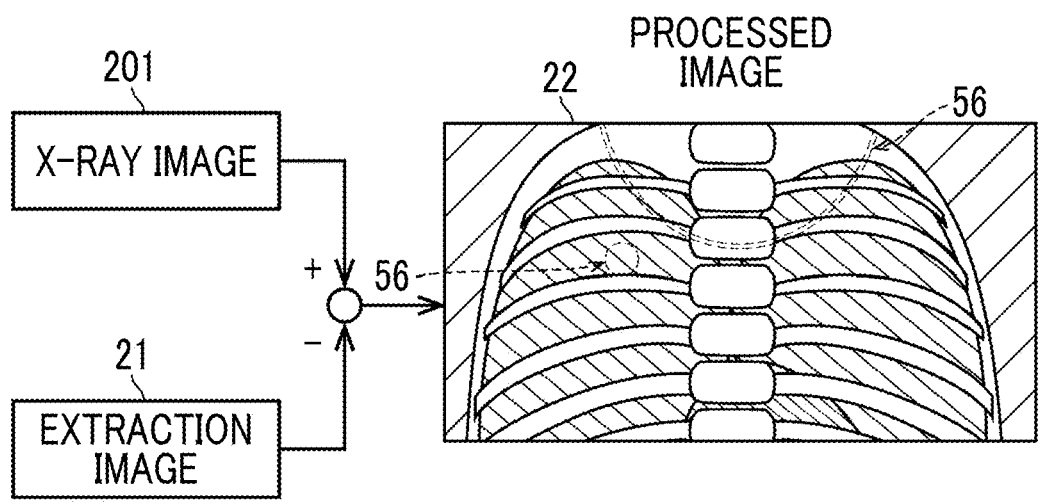
FIG. 22 is a diagram showing an example of the processed image in a case in which the image element is the clothing.

The image processing device 100 performs the weighting subtraction of the extraction image 21 generated by the trained model 40 on the X-ray image 201 acquired by the X-ray imaging device 200. As a result, as shown in FIG. 22, the processed image 22 in which the image element 50 of the clothing 56 is removed from the X-ray image 201 is generated. In FIG. 22, in order to describe the removal, for convenience, a part of the image element 50 of the removed clothing 56 is shown by a broken line.

<Scattered Ray Component>

Figure 23:
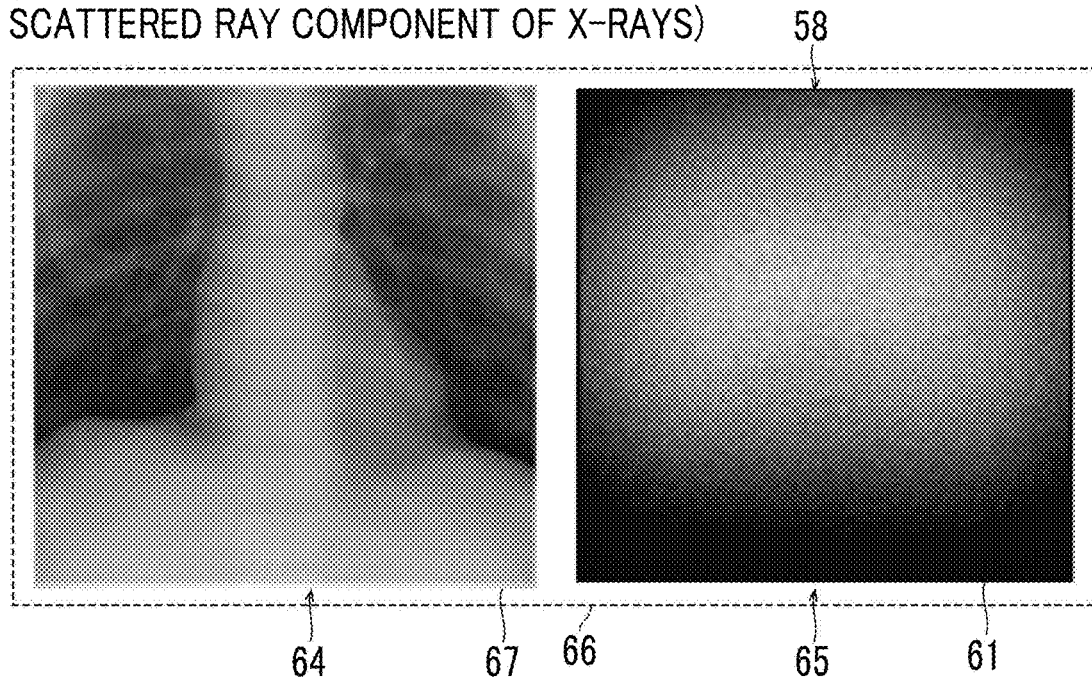
FIG. 23 is a diagram showing an example of the teacher input data and the teacher output data in a case in which the image element is a scattered ray component of X-rays.

FIG. 23 shows an example in which the image element 50 is the scattered ray component 58 of the X-rays.

The teacher input data 64 is the superimposed image 67 including the scattered ray component 58. In the reconstructed image 60 generated from the CT image data 80, the scattered ray component 58 is not included in a reconstruction arithmetic operation. The projection image 61 of only the scattered ray component 58 generated by the Monte Carlo simulation modeling an imaging environment of the input image is superimposed on the reconstructed image 60. As a result, the superimposed image 67 including the scattered ray component 58 is generated.

In the Monte Carlo simulation, for example, as shown in FIG. 2 (or FIG. 11), an imaging environment model 85 obtained by three-dimensionally modeling the imaging environment of the input image (X-ray image 201) from the X-ray irradiation unit 220 to the X-ray detector 230 is created. Moreover, each of X-ray photons emitted from the X-ray irradiation unit 220 and detected by the X-ray detector 230 is computed (simulated) as a probabilistic event using a random number. That is, in the simulation, the physical properties related to the projection direction of the X-rays, a shape (body shape) of the subject, and the interaction with photons are assumed. Moreover, the interaction, such as absorption and scattering phenomenon, that occurs when the X-ray photon passes through the subject is computed using a random number as the probabilistic event. In the Monte Carlo simulation, a predetermined number of photons is computed, and the projection image 61 formed by the X-ray photons detected by the virtual X-ray detector 230 is generated. The predetermined number of photons need only be a sufficient number for imaging, for example, about 10 billion.

Figure 25:
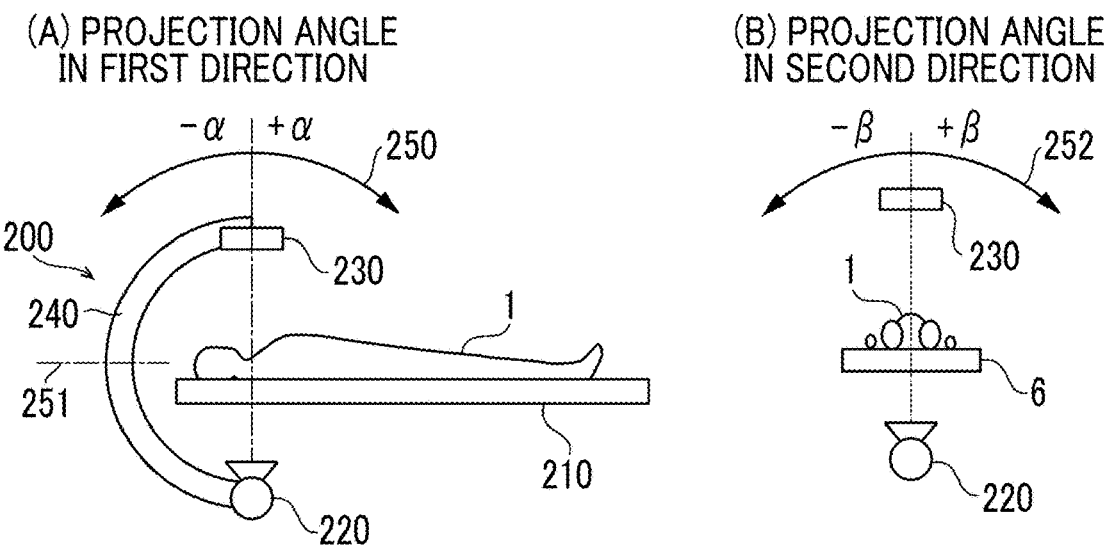
FIG. 25 is a diagram showing a projection angle range of the X-rays in a first direction (A) and a second direction (B) in a Monte Carlo simulation.

In the present embodiment, the plurality of the projection images 61 of the image element 50, which is the scattered ray component 58, are generated by changing the projection angle over a projection angle range capable of being imaged by the X-ray imaging device 200 in the imaging environment model 85. For example, in the example shown in FIG. 2, the projection direction can be changed to the first direction 250 and the second direction 252 by moving the C-arm 240. Therefore, as shown in FIG. 25, the projection image 61 by the Monte Carlo simulation is generated at a plurality of projection angles changed to different angle values over the entire projection angle range of $\pm\alpha$ degrees in the first direction 250 and $\pm\beta$, degrees in the second direction 252. The projection angle may be changed at equal intervals over the entire projection angle range, or may be a value randomly changed by a predetermined number in the projection angle range. Further, the projection image 61 may be generated at an angle value outside the projection angle range and near a limit of the projection angle ($\pm\alpha$ degrees, $\pm\beta$, degrees).

In addition, in the present embodiment, the plurality of projection images 61 of the image element 50, which is the scattered ray component 58, are generated by changing an energy spectrum of the virtual radiation source in the imaging environment model 85. That is, under a plurality of conditions in which the energy spectrum of the X-rays emitted by the X-ray irradiation unit 220 assumed as the imaging environment model 85 is changed to a different spectrum, the projection image 61 by the Monte Carlo simulation is created.

Figure 26:
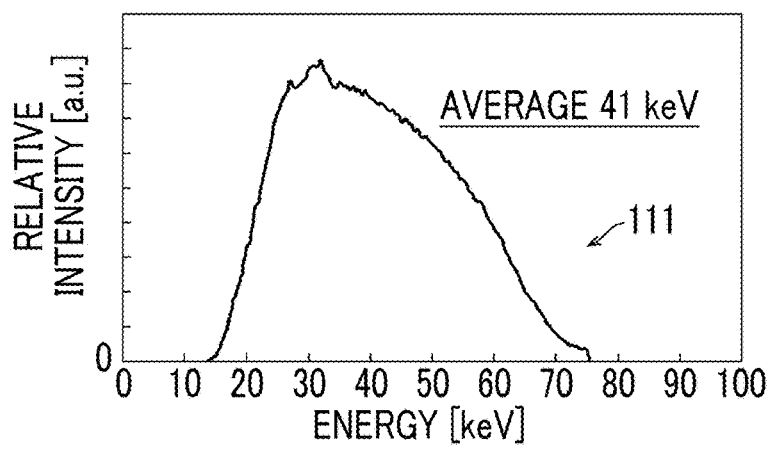
FIG. 26 is a diagram showing a first example of an energy spectrum of the X-rays in the Monte Carlo simulation.
Figure 27:
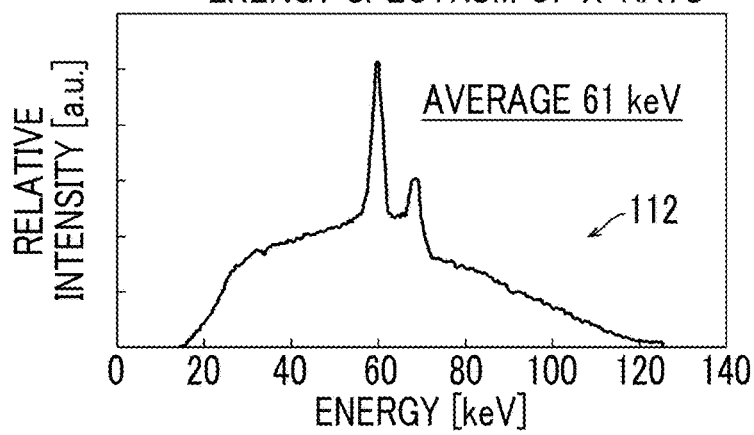
FIG. 27 is a diagram showing a second example of the energy spectrum of the X-rays in the Monte Carlo simulation.
Figure 28:
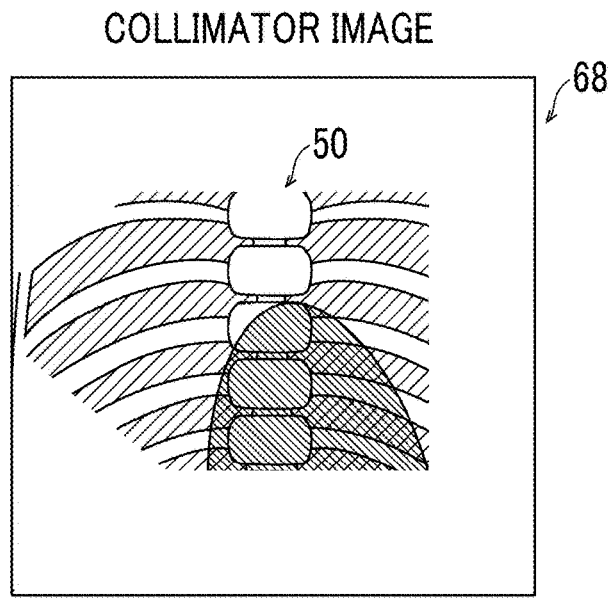
FIG. 28 is a diagram showing an example of a collimator image used for the teacher input data and the teacher output data.

Generally, as the photon energy of the X-rays is lower, it is more likely to be absorbed in the body of the subject, and it is less likely that the scattered ray component 58 is generated. As the photon energy of the X-rays is higher, it is less likely to be absorbed in the body of the subject, and it is more likely that the scattered ray component 58 is generated. Therefore, for example, the projection image 61 based on a first energy spectrum 111 shown in FIG. 26 and the projection image 61 based on a second energy spectrum 112 shown in FIG. 27 are created. The second energy spectrum 112 is a spectrum that has a relatively higher energy than the first energy spectrum 111. In FIGS. 26 and 27, the horizontal axis of the graph indicates the energy [keV] of X-ray photons, and the vertical axis of the graph indicates the relative intensity of the X-rays (that is, the number of detected X-ray photons).

It should be noted that, due to a difference in absorption spectra, a beam hardening phenomenon that is relatively biased toward a high energy side occurs in a process of detecting the energy spectrum of the X-rays emitted to the subject. The reconstructed image 60 generated from the CT image data 80 cannot simulate the change in image quality due to the beam hardening phenomenon, but the projection image 61 by the Monte Carlo simulation can simulate the influence of the beam hardening phenomenon.

FIG. 23 shows, as an example, the projection image 61 of the scattered ray component 58 due to Compton scattering obtained by the Monte Carlo simulation. In the present embodiment, the scattered ray component 58 other than Compton scattering, such as Rayleigh scattering, may be obtained. Further, the scattered ray component 58 due to multiple scattering, in addition to single scattering, may be obtained. The machine learning may be performed such that these various scattered ray components 58 are created as separate projection images 61 and separately extracted, or the machine learning may be performed such that the projection image 61 that collectively displays various scattered ray components 58 are created and various scattered ray components 58 are collectively extracted.

The teacher output data 65 is the projection image 61 including only the scattered ray component 58. As the teacher output data 65, the same data as the projection image 61 used to generate the superimposed image 67 is used.

Through the machine learning, the learning model LM is trained to generate the extraction image 21 in which the scattered ray component 58 is extracted, such as the teacher output data 65, from the input image, such as the teacher input data 64.

Figure 24:
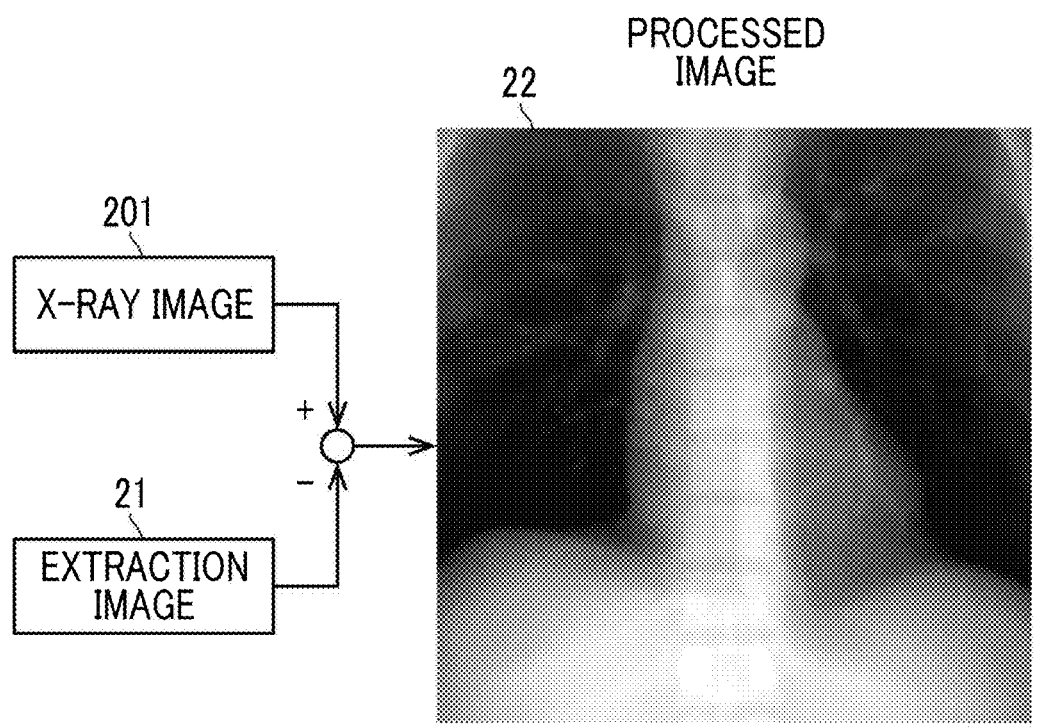
FIG. 24 is a diagram showing an example of the processed image in a case in which the image element is the scattered ray component of the X-rays.

The image processing device 100 performs the weighting subtraction of the extraction image 21 generated by the trained model 40 on the X-ray image 201 acquired by the X-ray imaging device 200. As a result, as shown in FIG. 24, the processed image 22 in which the image element 50 of the scattered ray component 58 is removed from the X-ray image 201 is generated. Since the scattered ray component 58 is a factor that lowers the contrast of the X-ray image, the contrast in the processed image 22 can be improved by removing the scattered ray component 58. The processed image 22 of FIG. 24 shows that the contrast is improved by removing the scattered ray component 58 from the X-ray image 201 of which the contrast is lowered by the scattered ray component 58 as in the teacher input data 64 of FIG. 23.

<Collimator Image>

In the present embodiment, a collimator image 68 of which an imaging range is limited by a collimator (not shown) provided in the X-ray imaging device 200 (X-ray irradiation unit 220) is included in a part of each teacher input data 64 and each teacher output data 65, which are created. In the collimator image 68, the image is formed only in a partial region of the image, and a region shielded by the collimator does not include the image information. A part of each teacher input data 64 and each teacher output data 65 includes a plurality of collimator images 68 in which the shape of the irradiation range of the X-rays (that is, image region) and the parameter of the image quality affected by the collimator are randomly made different by a simulation based on the image actually captured by the collimator. The parameters of the image quality affected by the collimator are a degree of transparency (contrast), blur of an edge, a content of the noise, and the like.

The collimator image 68 is generated, for example, by performing the image processing of removing the image part outside the simulated irradiation range and simulating the influence of the collimator on the superimposed image 67, the reconstructed image 60, and the projection image 61. The collimator image 68 may be generated from an image actually captured using the collimator. As a result, it is possible to improve the robustness of the processing of extracting the image element 50 with respect to the change in the irradiation range of the X-rays or the change in the image quality due to the use of the collimator.

As described above, the machine learning for each type of the image element 50 and the generation of the processed image 22 by the image processing device 100 are performed.

In each of the specific examples described above, for convenience of description, each image element 50 and the processed image 22 are described individually. However, in a case in which the processed image 22 is generated by the actual image processing device 100, the X-ray image 201 input to the image processing device 100 includes a plurality of image elements of the bone 53, the blood vessel 54, the device 55, the clothing 56, the noise 57, and the scattered ray component 58. The image processing device 100 generates the extraction image 21 obtained by extracting the individual image element 50 from the input X-ray image 201 using the trained model 40, and performs the inter-image arithmetic operation. As a result, the processed image 22 in which the enhancement processing or the removal processing is performed on each of the plurality of image elements 50 is generated.

For example, in the example shown in FIG. 7, N=6, the first extraction image 21-1 represents the bone 53, the second extraction image 21-2 represents the device 55, the third extraction image (21-3) represents the noise 57, the fourth extraction image (21-4) represents the blood vessel 54, the fifth extraction image (21-5) represents the clothing 56, and the sixth extraction image (21-6) represents the scattered ray component 58.

Some examples of the usage scene of the processed image 22 are shown.

For example, the processed image 22 is applied to the X-ray image of the front of the chest of the subject by simple X-ray imaging. In this case, in the processed image 22, the bone 53, the noise 57, the clothing 56, and the scattered ray component 58 are removed. Due to the removal the bone 53, the visibility of a region of interest, such as the heart and lungs, is improved. In addition, the visibility of the entire image is improved by removing the noise 57 and the scattered ray component 58. Since the image element 50 of the clothing 56 can be removed, the X-ray imaging can be performed in a case in which the subject does not remove the clothes, the accessory, or the like including metal or the like. As a result, useful effects, such as the improvement of the work efficiency and the reduction of waiting time of the subject, can be obtained in a case in which the X-ray imaging of a large number of subjects is continuously performed, such as in mass examination.

In addition, for example, the processed image 22 is applied to an X-ray fluoroscopic image in X-ray interventional radiology (IVR), such as catheter treatment using an X-ray blood vessel imaging device. In this case, in the processed image 22, the bone 53, the noise 57, and the scattered ray component 58 are removed. In the processed image 22, the device 55, such as the catheter, the guidewire, or the stent, and the blood vessel 54 are enhanced. Due to the removal of the bone 53, the noise 57, and the scattered ray component 58, the visibility of the fluoroscopic image is improved. Due to the enhancement of the device 55 and the blood vessel 54, the visibility of the region of interest or the device being operated in catheter treatment is improved.

Effect of Present Embodiment

In the present embodiment, the following effects can be obtained.

With the creation method of the trained model 40 according to the present embodiment, the superimposed image 67 obtained by superimposing the reconstructed image 60 obtained by reconstructing the CT image data 80 into the two-dimensional projective image on the two-dimensional projection image 61 generated from the three-dimensional model of the image element 50, which is the extraction target, by a simulation is used as the teacher input data 64, and the reconstructed image 60 or the projection image 61 is used as the teacher output data 65. As a result, even in a case in which the CT image data 80 does not include the image element 50, which is the extraction target, the machine learning can be performed using the image element 50, which is the extraction target, generated by a simulation. That is, the teacher data can be prepared without actually preparing the CT image data 80 including the image element 50 to be extracted. In addition, since the projection image 61 of the image element 50, which is the extraction target, is generated by the simulation, the teacher data can be prepared even for the image element 50 that is included in the CT image data 80, but is difficult to be separated and extracted. As a result, it is possible to efficiently create the trained model 40 for performing the image processing on various image elements 50 and even on the plurality of image elements 50.

With the image generation method and the image processing device 100 according to the present embodiment, the plurality of image elements 50 are separately extracted from the X-ray image 201 using the trained model 40 in which the processing of extracting the specific image element 50 from the input image has been learned, and the processed image 22 is generated by performing the inter-image arithmetic operation using the plurality of extraction images 21 extracted for the respective image elements 50, and the X-ray image 201. As a result, various image elements 50 can be separately extracted as the extraction image 21 from the input X-ray image 201, and each extraction image 21 can be freely added or subtracted from the X-ray image 201 in accordance with the type of the extraction image element 50. As a result, the image processing can be performed on various image elements 50 and even on the plurality of image elements 50.

In addition, in the example of the embodiment described above, a further effect can be obtained by the following configuration.

That is, in the present embodiment, a plurality of the superimposed images 67 are created for each of the plurality of image elements 50 different from each other, and the plurality of image elements 50 include the first element 51, which is the biological tissue, and the second element 52, which is the non-biological tissue. With this configuration, it is possible to create the trained model 40 that can perform, in a complex manner, the image processing with respect to the image element 50 of the biological tissue, such as the bone 53 or the blood vessel 54, and the image processing with respect to the image element 50 of the non-biological tissue, such as the device 55 introduced into the body or the clothing 56 worn by the subject. By using such a trained model 40 in the image processing device 100, it is possible to perform, in a complex manner, the image processing with respect to the image element 50 of the biological tissue and the image processing with respect to the image element 50 of the non-biological tissue.

In addition, in the present embodiment, the plurality of the superimposed images 67 are created for each of the plurality of image elements 50 different from each other, and the plurality of image elements 50 include at least a plurality of image elements of the bone 53, the blood vessel 54, the device 55 introduced into the body, the clothing 56, the noise 57, and the scattered ray component 58 of the X-rays. With this configuration, it is possible to create the trained model 40 that can perform the image processing on various image elements 50 in accordance with various usage scenes of the X-ray image 201 in a complex manner. By using such a trained model 40 in the image processing device 100, it is possible to perform the image processing on various image elements 50 in accordance with various usage scenes of the X-ray image 201 in a complex manner.

In addition, in the present embodiment, the image element 50 includes the device 55 having a linear shape or a tubular shape, the projection image 61 of the image element 50 is generated by simulating a shape of the three-dimensional model of the device 55 with a curve generated based on a random coordinate value. With this configuration, the teacher data for learning the image element 50 of the device 55, which is long and bends into various shapes, such as the guidewire and the catheter, can be generated in a large amount in various shapes by a simulation. As a result, efficient machine learning can be performed without actually preparing a large amount of the three-dimensional CT data in a state in which the device 55 is disposed in the body of the subject.

In addition, in the present embodiment, the image element 50 includes the blood vessel 54, the projection image 61 of the image element 50 is generated by a simulation that randomly changes a shape of the three-dimensional model of the blood vessel 54. With this configuration, the teacher data for learning the image element 50 of the blood vessel 54 that is long and bends into a complicated shape can be generated by a simulation in a large amount and including various individual differences. As a result, efficient machine learning can be performed without preparing a large amount of the three-dimensional CT data of various subjects.

In addition, in the present embodiment, the image element 50 includes the scattered ray component 58 of the X-rays, and the projection image 61 of the image element 50 is generated by the Monte Carlo simulation modeling the imaging environment of the input image. With this configuration, the projection image 61 of the scattered ray component 58 of the X-rays, which is difficult to be separated and extracted from the actual three-dimensional CT data or the two-dimensional X-ray image 201, can be generated by the Monte Carlo simulation. The image processing of removing the scattered ray component 58 from the X-ray image 201 obtained by actually imaging the subject by creating the trained model 40 that extracts the scattered ray component 58 using the projection image 61 generated in this way can be realized without performing complicated high-load computing processing, such as the Monte Carlo simulation. Therefore, for example, it is possible to effectively improve the contrast in the vicinity of the abdomen or the bone part, which is greatly affected by the scattered ray component 58. In addition, for example, in the X-ray imaging, it is possible to perform the imaging without using an X-ray absorption grid used to reduce the influence of the scattered ray component 58, and to remove the scattered ray component 58 by the image processing. In that case, since an X-ray dose can be reduced by an amount that the X-ray absorption grid is not used, an exposure dose of the subject can be effectively reduced.

In addition, in the present embodiment, the plurality of the projection images 61 of the image element 50 are generated by changing the projection angle over the projection angle range (±α, ±β) capable of being imaged by the X-ray imaging device 200 in the imaging environment model 85. With this configuration, it is possible to create a highly versatile trained model 40 that can effectively extract the scattered ray component 58 even in a case in which the X-ray imaging is performed at various projection angles in the X-ray interventional radiology or the X-ray imaging is performed while changing the projection angles, in addition to the imaging is performed only from a specific projection direction (front of the chest, side of the chest, or the like), such as the simple X-ray imaging.

In addition, in the present embodiment, the plurality of projection images 61 of the image element 50 are generated by changing an energy spectrum of the virtual radiation source in the imaging environment model 85. In an actual medical field, the X-ray imaging is performed under various imaging conditions having different energy spectra in accordance with the imaging part or the like. However, with the configuration described above, it is possible to create a highly versatile trained model 40 that can effectively extract the scattered ray component 58 even in a case in which such an X-ray image 201 is captured with various energy spectra.

In addition, in the present embodiment, the machine learning includes inputting the teacher input data 64 and the teacher output data 65 created for each image element 50 to one learning model LM, and the trained model 40 is configured to extract the plurality of image elements 50 from the input image without duplication, and output the extracted plurality of image elements 50 and the residual image element 59 remaining after extraction, respectively. With this configuration, it is possible to provide the trained model 40 that can extract the image element 50 such that the original input image is returned in a case in which all the extracted plurality of image elements 50 and the residual image element 59 are added. That is, even in a case in which the plurality of image elements 50 are extracted from one X-ray image 201, a loss of the image information included in the X-ray image 201 or unintended increase in the image information does not occur. Since a doctor or the like who makes a diagnosis using the X-ray image 201 finds the basis of the diagnosis in the image information included in the original image even in a case in which various image processing for improving the visibility are performed, it is possible to provide the reliable image for the doctor or the like even in a case in which the complex image processing is performed, with the trained model 40 that can extract the image element 50 such that the loss of the image information does not occur.

In addition, in the present embodiment, the image processing is performed separately on a part or all of the plurality of extraction images 21, and the processed image 22 is generated by the inter-image arithmetic operation between the plurality of extraction images 21 after the image processing, and the X-ray image 201. With this configuration, by utilizing the fact that the plurality of image elements 50 can be separately extracted using the trained model 40, the image processing, such as the correction processing or the complementation processing, can be independently performed on the extraction image 21 of each extraction image element 50. Here, for example, in a case in which an attempt is made to perform the image processing that acts only on the specific image element 50 on the X-ray image 201 before extraction, the image processing algorithm is complicated and heavy, and the image elements 50 other than the specific image element 50 may be adversely affected. On the other hand, in a case in which the image processing is performed on the extraction image 21, since there is no other image element 50, high image processing accuracy can be obtained by simply performing simple filtering processing on the entire extraction image 21. Moreover, by performing the inter-image arithmetic operation using the extraction image 21 after the image processing, the processed image 22 in which the highly accurate image processing limited to the individual image element 50 is performed in addition to simply enhancing or removing the plurality of image elements 50 can be easily generated.

In addition, in the present embodiment, the inter-image arithmetic operation includes the weighting addition or the weighting subtraction of the individual extraction image 21 with respect to the X-ray image 201. With this configuration, it is possible to obtain the processed image 22 in which the extracted plurality of image elements 50 are individually enhanced or removed one by one. In addition, since the degree of enhancement or the degree of removal of the individual image element 50 can be appropriately set by adjusting the weight coefficient 23, it is possible to generate the processed image 22 that can obtain high visibility for the required image element 50 in accordance with various usage scenes of the X-ray image 201.

Modification Example

It should be noted that the embodiment disclosed this time is an exemplary example in all respects and are not considered to be restrictive. The scope of the present invention is shown by the scope of claims, not the description of the above embodiment, and further includes all changes (modification examples) within the meaning and scope equivalent to the scope of claims.

For example, in the embodiment described above, an example is shown in which the device that performs the machine learning (learning device 300) and the image processing device 100 are separate devices, but the present invention is not limited thereto. In the present invention, the machine learning may be performed in the image processing device. In addition, the learning device 300 may be configured by a server computer provided on the cloud.

Figure 29:
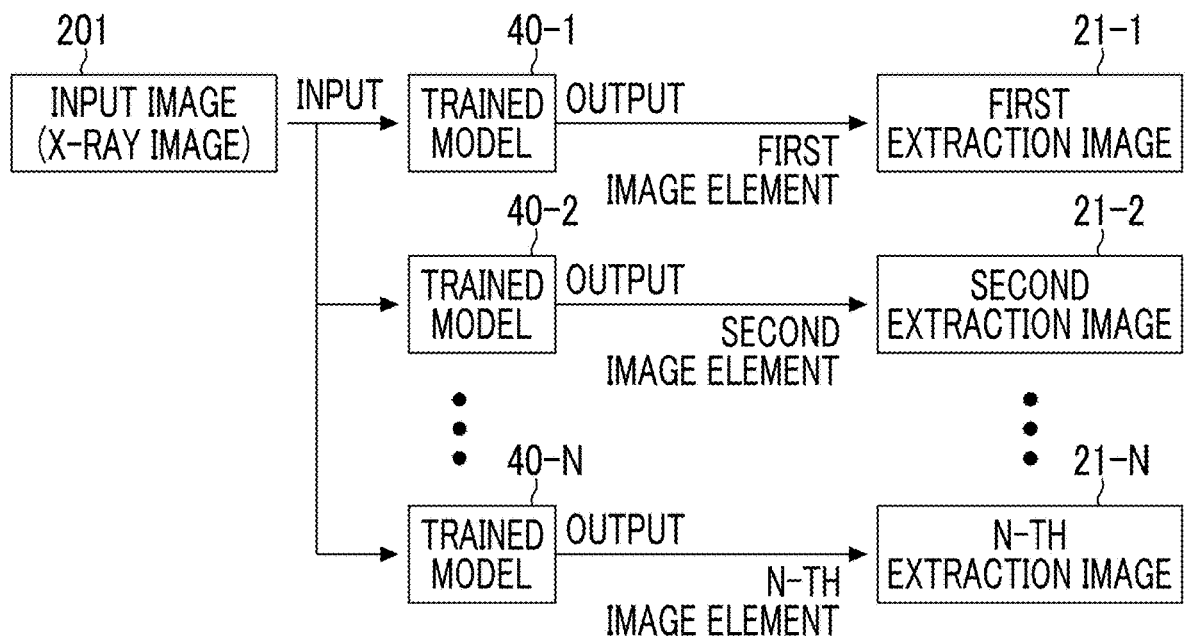
FIG. 29 is a diagram showing an example of extracting the image elements from a plurality of trained models.

In addition, in the embodiment described above (see FIGS. 5 to 7), an example in which the plurality of image elements 50 are extracted by one trained model 40 is shown, but the present invention is not limited thereto. In the present invention, the plurality of image elements 50 may be extracted by a plurality of trained models. For example, as shown in FIG. 29, one trained model 40 may be provided for each image element 50 to be extracted. In FIG. 29, a trained model 40-1, a trained model 40-2, . . . , and a trained model 40-N are provided. One trained model 40 extracts one (one type of) image element 50. In addition, a plurality of trained models 40 created to extract the plurality of image elements 50 may be provided.

In addition, in the embodiment described above, an example is shown in which the plurality of image elements 50 include at least a plurality of image elements of the bone 53, the blood vessel 54, the device 55, the clothing 56, the noise 57, and the scattered ray component 58, but the present invention is not limited thereto. The image element 50 may include the image elements other than the bone 53, the blood vessel 54, the device 55, the clothing 56, the noise 57, and the scattered ray component 58. The image element 50 may be a specific structural part, such as a specific organ in the body. In addition, for example, the image element 50 of the bone at the specific part among the bones 53 or the image element 50 of the blood vessel at the specific part among the blood vessels 54 may be separately extracted from other bones or other blood vessels. The image element 50 does not have to include the bone 53, the blood vessel 54, the device 55, the clothing 56, the noise 57, and the scattered ray component 58.

In addition, in the embodiment described above, an example is shown in which the removal processing is performed on the bone 53 and the enhancement processing is performed the blood vessel 54 and the device 55 by the inter-image arithmetic operation, but the present invention is not limited thereto. The enhancement processing may be performed on the bone 53, or the removal processing may be performed on one or both of the blood vessel 54 and the device 55.

In addition, in the embodiment described above, two examples of the weighting addition and the weighting subtraction are shown as examples of the inter-image arithmetic operation, but the present invention is not limited thereto. The inter-image arithmetic operation may be addition or subtraction without the weight coefficient. The enhancement processing of the image element 50 may be performed by multiplication with the weight coefficient or without the weight coefficient. The removal processing of the image element 50 may be performed by division with the weight coefficient or without the weight coefficient.

ASPECT

It will be understood by those skilled in the art that the exemplary embodiment described above is a specific example of the following aspects.

(Item 1)

A creation method of a trained model, the method including generating a reconstructed image obtained by reconstructing three-dimensional X-ray image data into a two-dimensional projective image, generating a two-dimensional projection image from a three-dimensional model of an image element, which is an extraction target, by a simulation, superimposing the projection image of the image element on the reconstructed image to generate a superimposed image, and creating a trained model that performs processing of extracting the image element included in an input image, by performing machine learning using the superimposed image as teacher input data and the reconstructed image or the projection image as teacher output data.

(Item 2)

The creation method of a trained model according to item 1, in which a plurality of the superimposed images are created for each of a plurality of image elements different from each other, and the plurality of image elements include a first element, which is a biological tissue, and a second element, which is a non-biological tissue.

(Item 3)

The creation method of a trained model according to item 1, in which a plurality of the superimposed images are created for each of a plurality of image elements different from each other, and the plurality of image elements include at least a plurality of image elements of a bone, a blood vessel, a device introduced into a body, clothing, a noise, and a scattered ray component of X-rays.

(Item 4)

The creation method of a trained model according to item 1, in which the image element includes a device having a linear shape or a tubular shape, and the projection image of the image element is generated by simulating a shape of a three-dimensional model of the device with a curve generated based on a random coordinate value.

(Item 5)

The creation method of a trained model according to item 1, in which the image element includes a blood vessel, and the projection image of the image element is generated by a simulation that randomly changes a shape of a three-dimensional model of the blood vessel.

(Item 6)

The creation method of a trained model according to item 1, in which the image element includes a scattered ray component of X-rays, and the projection image of the image element is generated by a Monte Carlo simulation that models an imaging environment of the input image.

(Item 7)

The creation method of a trained model according to item 6, in which a plurality of the projection images of the image element are generated by changing a projection angle over a projection angle range capable of being imaged by an X-ray imaging device in an imaging environment model.

(Item 8)

The creation method of a trained model according to item 6, in which a plurality of the projection images of the image element are generated by changing an energy spectrum of a virtual radiation source in an imaging environment model.

(Item 9)

The creation method of a trained model according to item 1, in which the machine learning includes inputting the teacher input data and the teacher output data created for each image element to one learning model, and the trained model is configured to extract the plurality of image elements from the input image without duplication, and output the extracted plurality of image elements and a residual image element remaining after extraction, respectively.

(Item 10)

An image generation method including separately extracting a plurality of image elements from an X-ray image using a trained model in which processing of extracting a specific image element from an input image has been learned, and generating a processed image in which image processing is performed on each image element included in the X-ray image, by performing an inter-image arithmetic operation using a plurality of extraction images extracted for the respective image elements, and the X-ray image.

(Item 11)

The image generation method according to item 10, in which the image processing includes enhancement processing or removal processing.

(Item 12)

The image generation method according to item 10, in which the plurality of image elements include a first element, which is a biological tissue, and a second element, which is a non-biological tissue.

(Item 13)

The image generation method according to item 10, in which the plurality of image elements include at least a plurality of image elements of a bone, a blood vessel, a device introduced into a body, clothing, a noise, and a scattered ray component of X-rays.

(Item 14)

The image generation method according to item 10, in which the image processing is performed separately on a part or all of the plurality of extraction images, and the processed image is generated by the inter-image arithmetic operation between the plurality of extraction images after the image processing, and the X-ray image.

(Item 15)

The image generation method according to item 10, in which the inter-image arithmetic operation includes weighting addition or weighting subtraction of an individual extraction image with respect to the X-ray image.

(Item 16)

The image generation method according to item 10, in which the trained model is configured to extract the plurality of image elements from the input image without duplication, and output the extracted plurality of image elements and a residual image element remaining after extraction, respectively.

(Item 17)

The image generation method according to item 10, in which the trained model is created in advance through machine learning using a reconstructed image obtained by reconstructing three-dimensional image data into a two-dimensional projective image, and a projection image created from a three-dimensional model of the image element by a simulation.

(Item 18)

An image processing device including an image acquisition unit that acquires an X-ray image, an extraction processing unit that separately extracts a plurality of image elements from the X-ray image using a trained model in which processing of extracting a specific image element from an input image has been learned, and an image generation unit that generates a processed image in which image processing is performed on each image element included in the X-ray image, by performing an inter-image arithmetic operation using a plurality of extraction images extracted for the respective image elements, and the X-ray image.

REFERENCE SIGNS LIST

- 10: Image acquisition unit
- 20: Extraction processing unit
- 21 (21-1, 21-2, 21-N): extraction image
- 22: Processed image
- 30: Image generation unit
- 40 (40-1, 40-2, 40-N): Trained model
- 50: Image element
- 51: First element
- 52: Second element
- 53: bone
- 54: Blood vessel
- 55: device
- 56: Clothing
- 57: Noise
- 58: Scattered ray component
- 59: Residual image element
- 60: Reconstructed image
- 61: Projection image
- 64: Teacher input data
- 65: Teacher output data
- 67: Superimposed image
- 80: CT image data (three-dimensional X-ray image data)
- 85: Imaging environment model
- 100: Image processing device
- 111: First energy spectrum (energy spectrum)
- 112: Second energy spectrum (energy spectrum)
- 200: X-ray imaging device
- 201: X-ray image
- LM: learning model

The invention claimed is:

1. A creation method of a trained model, the method comprising:
    generating a reconstructed image obtained by reconstructing three-dimensional X-ray image data into a two-dimensional projective image;
    generating a two-dimensional projection image from a three-dimensional model of an image element, which is an extraction target, by a simulation;
    superimposing the projection image of the image element on the reconstructed image to generate a superimposed image; and
    creating a trained model that performs processing of extracting a plurality of the image element included in an input image and generating a plurality of extraction images which the plurality of the image element are reflected therein, by performing machine learning using the superimposed image as teacher input data and the reconstructed image or the projection image as teacher output data.

2. The creation method of a trained model according to claim 1,
    wherein a plurality of the superimposed images are created for each of a plurality of image elements different from each other, and
    the plurality of image elements include
        a first element, which is a biological tissue, and a second element, which is a non-biological tissue, or
        at least a plurality of image elements of a bone, a blood vessel, a device introduced into a body, clothing, a noise, and a scattered ray component of X-rays.

3. The creation method of a trained model according to claim 1,
    wherein the image element includes a device having a linear shape or a tubular shape, and
    the projection image of the image element is generated by simulating a shape of a three-dimensional model of the device with a curve generated based on a random coordinate value.

4. The creation method of a trained model according to claim 1,
    wherein the image element includes a blood vessel, and
    the projection image of the image element is generated by a simulation that randomly changes a shape of a three-dimensional model of the blood vessel.

5. The creation method of a trained model according to claim 1,
    wherein the image element includes a scattered ray component of X-rays, and
    the projection image of the image element is generated by a Monte Carlo simulation that models an imaging environment of the input image.

6. The creation method of a trained model according to claim 5,
    wherein a plurality of the projection images of the image element are generated
        by changing a projection angle over a projection angle range capable of being imaged by an X-ray imaging device in an imaging environment model, or
        by changing an energy spectrum of a virtual radiation source in an imaging environment model.

7. The creation method of a trained model according to claim 1,
    wherein the machine learning includes inputting the teacher input data and the teacher output data created for each image element to one learning model, and the trained model is configured to extract the plurality of image elements from the input image without duplication, and output the extracted plurality of image elements and a residual image element remaining after extraction, respectively.

8. An image generation method comprising:
separately generating a plurality of extraction images by a plurality of image elements from an X-ray image using a trained model in which processing of extracting an image element from an input image has been learned; and
generating a processed image in which image processing is performed on each image element included in the X-ray image, by weighting each of the plurality of extraction images and adding or subtracting the weighted plurality of extraction images to or from the X-ray image.

9. The image generation method according to claim 8, wherein the image processing includes enhancement processing or removal processing.

10. The image generation method according to claim 8, wherein the plurality of image elements include
    a first element, which is a biological tissue, and a second element, which is a non-biological tissue, or
    at least a plurality of image elements of a bone, a blood vessel, a device introduced into a body, clothing, a noise, and a scattered ray component of X-rays.

11. The image generation method according to claim 8, wherein the image processing is performed separately on a part or all of the plurality of extraction images, and the processed image is generated by the plurality of extraction images after the image processing, and the X-ray image.

12. The image generation method according to claim 8, wherein the trained model is configured to extract the plurality of image elements from the input image without duplication, and output the extracted plurality of image elements and a residual image element remaining after extraction, respectively.

13. The image generation method according to claim 8, wherein the trained model is created in advance through machine learning using a reconstructed image obtained by reconstructing three-dimensional image data into a two-dimensional projective image, and a projection image created from a three-dimensional model of the image element by a simulation.

14. An image processing device comprising:
an image acquisition unit that acquires an X-ray image;
an extraction processing unit that separately generates a plurality of extraction images by a plurality of image elements from the X-ray image using a trained model in which processing of extracting an image element from an input image has been learned; and
an image generation unit that generates a processed image in which image processing is performed on each image element included in the X-ray image, by weighting each of the plurality of extraction images and adding or subtracting the weighted plurality of extraction images to or from the X-ray image.

15. A creation method of a trained model, the method comprising:
generating a reconstructed image obtained by reconstructing three-dimensional X-ray image data into a two-dimensional projective image;
generating a two-dimensional projection image by simulating a shape of a three-dimensional model of an image element of a linear or tubular shape curved device, which is an extraction target, with a curve;
superimposing the projection image of the image element on the reconstructed image to generate a superimposed image; and
creating a trained model used in a process of extracting the image element included in an input image, by performing machine learning using the superimposed image as teacher input data and the reconstructed image or the projection image as teacher output data.

* * * * *